US012570990B2

(12) United States Patent
Janssen et al.

(10) Patent No.: US 12,570,990 B2
(45) Date of Patent: Mar. 10, 2026

(54) LARGE VECTORS AND METHODS FOR HIGH-YIELD PRODUCTION

(71) Applicant: Katholieke Universiteit Leuven, Leuven (BE)

(72) Inventors: Melody Janssen, Amsterdam (NL); Joeri Auwerx, Bierbeek (BE); Kai Dallmeier, Kessel-Lo (BE); Nicolas Ongenae, Waremme (BE); Cédric Vansalen, Mechelen (BE); Nesya Goris, Schoten (BE)

(73) Assignee: Katholieke Universiteit Leuven, Leuven (BE)

( * ) Notice: Subject to any disclaimer, the term of this patent is extended or adjusted under 35 U.S.C. 154(b) by 944 days.

(21) Appl. No.: 17/636,175

(22) PCT Filed: Sep. 25, 2020

(86) PCT No.: PCT/EP2020/076864
§ 371 (c)(1),
(2) Date: Feb. 17, 2022

(87) PCT Pub. No.: WO2021/058722
PCT Pub. Date: Apr. 1, 2021

(65) Prior Publication Data
US 2023/0183718 A1     Jun. 15, 2023

(30) Foreign Application Priority Data

Sep. 25, 2019    (EP) .................................... 19199473

(51) Int. Cl.
*C07H 21/02*         (2006.01)
*C12N 15/70*         (2006.01)
*C12N 15/72*         (2006.01)

(52) U.S. Cl.
CPC ........ *C12N 15/72* (2013.01); *C12N 2800/101* (2013.01); *C12N 2820/002* (2013.01); *C12N 2820/55* (2013.01)

(58) Field of Classification Search
CPC combination set(s) only.
See application file for complete search history.

(56) References Cited

U.S. PATENT DOCUMENTS

2016/0206723 A1    7/2016    Dallmeier et al.
2019/0111125 A1    4/2019    Dallmeier et al.

FOREIGN PATENT DOCUMENTS

| CN | 105229153 A | 1/2016 |
| EP | 0179786 B1 | 5/1990 |
| WO | 2014174078 A1 | 10/2014 |

OTHER PUBLICATIONS

PCT International Search Report and Written Opinion dated Dec. 10, 2020 in connection with PCT International Patent Application No. PCT/EP2020/076864.
Dieudonné Buh Kum et al: "Limited evolution of the yellow fever virus 17d in a mouse infection model," Emerging Microbes & Infections, vol. 8, No. 1, Jan. 1, 2019 (Jan. 1, 2019), pp. 1734-1746, XP055667486.
Johan Neyts et al: "A novel vaccine technology platform Plasmid Launched Live Attenuated Virus (PLLAV) vaccines," Rega Ku Leuven, Jan. 1, 2018 (Jan. 1, 2018), see p. 9, XP055627733, Retrieved from the Internet: URL:https://rega.kuleuven.be/cmt/jn/downloads-1/johan-neyts-2018-presentation-on-pplav.pdf [retrieved on Jan. 10, 2019], 27 pages.
Jadwiga Wild et al: "Conditionally amplifiable BACs: switching from single-copy to high-copy vectors and genomic clones," Genome Research, Cold Spring Harbor Laboratory Press, U.S., vol. 2512, No. 9, Sep. 1, 2002 (Sep. 1, 2002), pp. 1434-1444, XP002463965.
Jadwiga Wild et al: "Single-copy/high-copy (SC/HC) pBAC/oriV novel vectors for genomics and gene expression," Plasmid, New York, NY, U.S., vol. 45, No. 2, Mar. 1, 2001 (Mar. 1, 2001), pp. 142-143, XP009097970.
Panayotatos et al., DNA replication regulated by the priming promoter, Nucleic Acids Research, Mar. 2, 1984 1 (Mar. 2, 1984), vol. 12(8):2641-2648.
Chinese Office Action as Issued On Oct. 22, 2025 In Respect of the Counterpart Chinese Patent Application No. 202080066336.1 And Its English Translation.
Manel Camps: Modulation of ColE1-Like Plasmid Replication for Recombinant Gene Expression, "Recent Patents on DNA & Gene Sequences", 4, 58-73 (16 pp), Jan. 31, 2010 (Jan. 31, 2010).

*Primary Examiner* — Jennifer E Graser
(74) *Attorney, Agent, or Firm* — Amster, Rothstein & Ebenstein LLP

(57) ABSTRACT

Provided herein are methods for the production of a vector with a size of at least 16 kb from bacterial cells comprising the consecutive steps of a) obtaining bacterial cells comprising a vector with a size of at least 16 kb, comprising an inducible origin of replication, b) inoculating culture medium with the bacterial cells comprising the vector, c) culturing the bacterial cells in the culture medium, d) adding one or more inducers of said inducible origin of replication to the culture medium when the bacterial culture has reached an optical density at 600 nm (OD600) of at least 20, e) further culturing the bacterial cells in the culture medium, f) optionally separating the bacterial cells from the culture medium, and g) recovering the plasmid from the bacterial cells. Also provided herein are vectors with a size of at least 16 kb comprising an inducible origin of replication for use in such methods.

14 Claims, 7 Drawing Sheets

Specification includes a Sequence Listing.

FIG 1.
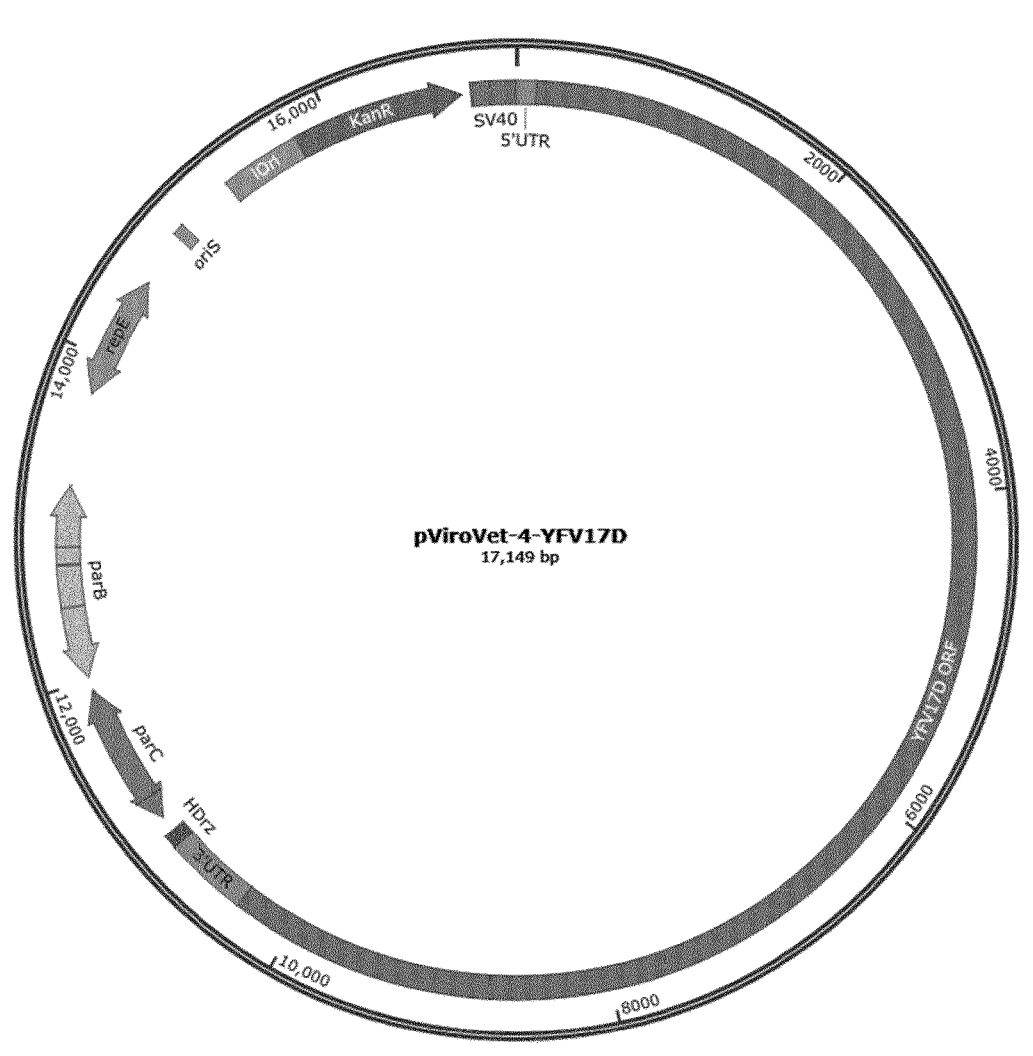
iOri:
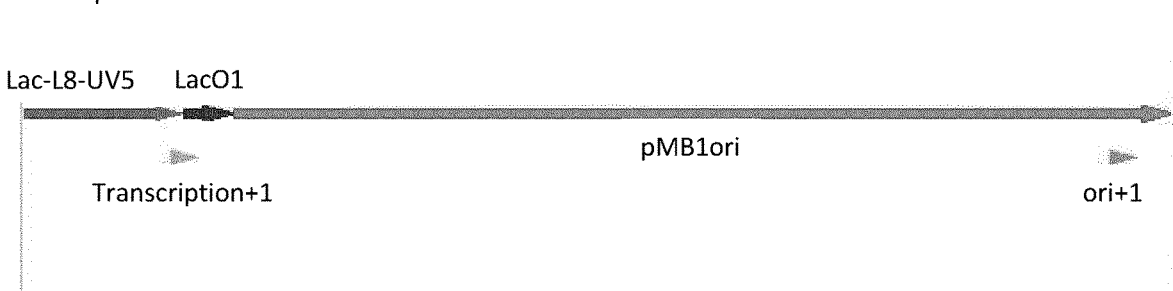

FIG 2.

**Full pMB1 (ColE1) ori (including RNAII\*, RNAI, RNAIp and RNAIIp)**    SEQ ID NO 10

GTAGAAAAGATCAAAGGATCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACTCTGTAGCACC
GCCTACATACCTCGCTCTGCTAATCCTGTTACCAGTGGCTGCTGCCAGTGGCGATAAGTCGTGTCTTACCGGGT
TGGACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCTGACTTGAGCGTCGATTTTTGTGA
TGCTCGTCAGGGGGGCGGAGCCTATGGAAAAACGCCAGCAACGCGGCCTTTTTACGGTTCCT

| Name | type | location |
|---|---|---|
| RNAII* | misc_feature | 238..644 |
| ori +1 | misc_feature | 624..624 |
| RNAI -35 | -35_signal | 201..206 |
| RNAI -10 | -10_signal | 177..182 |
| RNAI +1 | misc_signal | 170..170 |
| RNAII -10 (original) | -10_signal | 47..52 |
| RNAII -35 (original) | -35_signal | 24..29 |
| RNAII +1 (original) | misc_feature | 60..60 |

**Full iOri (including lac-L8-UV5, lacO1 and RNAII\* including mutations)**    SEQ ID NO 9

ATGTAAGTTAGCTCATTCATTAGGCACCCCAGGCTTTACACTTTATGCTTCCGGCTCGTATAATGTGTGGAattgt
gagcggataacaattCTGCTAATCCTGTTACCAGTGGCTGCTGCCAGTGGCGATAAGTCGTGTCTTACCGGGTTGG
ACTCAAGACGATAGTTACCGGATGAGGCGCAGCGGTCGGGCTGAACGGGGGGTTCGTGCACACAGCCCAGC
TTGGAGCGAACGACCTACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCACGAGGGAGCTTCCAG
GGGGAAACGCCTGGTATCTTTATAGTCCTGTTGGGTTTCGCCACCTCTGACTTGAGCGTCGATTTTTGTGATGC
TCGTCAGGGGGGCGGAGCCTATGGAAAAACGCCAGCAACGCGGCCTTTTTACGGTTCCT

| Name | type | location |
|---|---|---|
| lac-L8-UV5 | promoter | 1..70 |
| LacO1 | misc_feature | 71..91 |
| RNAII* | misc_feature | 92..498 |
| C->T mutation | modified_base | 397..397 |
| A->G mutation | modified_base | 176..176 |
| transcription+1 | misc_feature | 71..71 |
| ori +1 | misc_feature | 478..478 |

(A) pMB1/ColE1 Ori (B) iOri

FIG 9.

RNAI (SEQ ID NO 1):

ACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTAC

RNAI promoter (SEQ ID NO 2):

AGCGAGGTATGTAGGCGGTGCTACAGAGTTCTTGAAGTGGTGGCCTAACTACGGCTACAC
TAGAAGG endogenous promoter of the RNAII pre-primer (SEQ ID NO 3):

GTAGAAAAGATCAAAGGATCTTCTTGAGATCCTTTTTTTCTGCGCGTAATCTGCTGCTT

*lac* promoter (SEQ ID NO 4):

ATGTAAGTTAGCTCATTCATTAGGCACCCCAGGCTTTACACTTTATGCTTCCGGCTCGTAT
AATGTGTGG

LacO1 operator (SEQ ID NO 5):

attgtgagcggataacaatt truncated RNAII pre-primer (SEQ ID NO 6):

CTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGC
ACACAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGCGGCA
GGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCT

Mutated truncated RNAII pre-primer (SEQ ID NO 7):

CTGCTAATCCTGTTACCAGTGGCTGCTGCCAGTGGCGATAAGTCGTGTCTTACCGGGTTGG
ACTCAAGACGATAGTTACCGGAT<u>G</u>AGGCGCAGCGGTCGGGCTGAACGGGGGGTTCGTGC
ACACAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGCGGCA
GGGTCGGAACAGGAGAGCGCACGAGGGAGCTTCCAGGGGGAAACGCCTGGTATCTTTAT
AGTCCTGT<u>T</u>GGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCT

FIG 9. (continued)

iOri with truncated RNAII pre-primer (SEQ ID NO 8)

ATGTAAGTTAGCTCATTCATTAGGCACCCCAGGCTTTACACTTTATGCTTCCGGCTCGTAT
AATGTGTGGAattgtgagcggataacaattCTGCTAATCCTGTTACCAGTGGCTGCTGCCAGTGGCGA
TAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGA
TTTTTGTGATGCTCGTCAGGGGGGCGGAGCCTATGGAAAAACGCCAGCAACGCGGCCTTT
TTACGGTTCCT iOri with mutated truncated RNAII pre-primer (SEQ ID NO 9)

ATGTAAGTTAGCTCATTCATTAGGCACCCCAGGCTTTACACTTTATGCTTCCGGCTCGTAT
AATGTGTGGAattgtgagcggataacaattCTGCTAATCCTGTTACCAGTGGCTGCTGCCAGTGGCGA
TAAGTCGTGTCTTACCGGGTTGGACTCAAGACGATAGTTACCGGAT<u>G</u>AGGCGCAGCGGTC
GGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTTCCAGG
GGGAAACGCCTGGTATCTTTATAGTCCTGT<u>T</u>GGGTTTCGCCACCTCTGACTTGAGCGTCGA
TTTTTGTGATGCTCGTCAGGGGGGCGGAGCCTATGGAAAAACGCCAGCAACGCGGCCTTT
TTACGGTTCCT

Full pMB1 (ColE1) ori (SEQ ID NO 10)

GTAGAAAAGATCAAAGGATCTTCTTGAGATCCTTTTTTTCTGCGCGTAATCTGCTGCTTGC
AAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTCCTTCTAGTGT
AGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTC
AAGACGATAGTTACCGGATAAGGCGCAGCGGTCGGGCTGAACGGGGGGTTCGTGCACAC
AGCCCAGCTTGGAGCGAACGACCTACACCGAACTGAGATACCTACAGCGTGAGCTATGA
GAAAGCGCCACGCTTCCCGAAGGGAGAAAGGCGGACAGGTATCCGGTAAGCGGCAGGGT
CGGAACAGGAGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCGTCAGGGGGGCG
GAGCCTATGGAAAAACGCCAGCAACGCGGCCTTTTTACGGTTCCT

LARGE VECTORS AND METHODS FOR HIGH-YIELD PRODUCTION

CROSS-REFERENCE TO RELATED APPLICATIONS

This application is a U.S. national stage entry under 35 U.S.C. § 371 of PCT International Patent Application No. PCT/EP2020/076864, filed Sep. 25, 2020, which claims priority to European Patent Application No. 19199473.0, filed Sep. 25, 2019, the contents of each of which are incorporated herein by reference in their entirety.

FIELD OF THE INVENTION

The present inventions relates to vectors and methods for high yield production of large vectors.

BACKGROUND OF THE INVENTION

Gene therapy and DNA vaccines are promising tools for the prevention, treatment and cure of diseases, such as cancer and acquired immunodeficiency syndrome (AIDS). Gene therapy and DNA vaccines require large quantities of highly purified plasmid DNA (pDNA) that should be homogeneous with respect to structural form and DNA sequence. Additionally, gene therapy and DNA vaccines, such as DNA vaccines against complex pathogens, require plasmids which are able to tolerate large genomic DNA inserts. For biopharmaceutical use, yield and quality are the major drivers for the manufacturing process of plasmids. In the quest for an increase in yield, plasmids were developed which would result in high copy numbers, meaning that they would lead to multiple copies of plasmid per cell (>500 copies per cell. e.g. pUC18, pUC19 vectors). Such high copies of plasmid per cell can be achieved with small plasmids (<10 kb). However, the larger the plasmid, the slower replication will occur due to a high metabolic burden on the bacterial cell. The bacterial cell will respond to the metabolic burden by introducing mutations into the plasmid. As a result thereof, the quality of the plasmid DNA will decrease. This can be optimized by using low copy number vectors, such as bacterial artificial chromosomes (BACs), which are the preferred plasmid for maintaining large genomic DNA fragments as they can stably maintain individual DNA fragments in a single-copy (SC) vector in the host cells, even after more than 100 generations of serial bacterial growth.

Recent advances relate to the optimalisation of the copy number of BACs. For example, WO2014174078 describes BACs comprising an inducible bacterial origin of replication (ori) sequence for amplification of the BAC to more than 10 copies per bacterial cell. However, these BACs do not allow obtaining high, commercially viable, yields of BACs. As a result thereof, very large scale cultures are required to obtain substantial amount of BAC.

It is essential to develop new vectors and protocols to obtain high-quality plasmids with high yields.

Conditional amplification of vectors comprising an inducible bacterial origin of replication (ori) sequence in bacteria has been described in the art. The induction of amplification is typically performed in the early exponential growth phase of the bacteria, more particularly, in the early log(arithmic) phase of the bacterial growth curve (i.e. at low OD) (Wild et al. 2002, Genome Research 12:1434-1444).

SUMMARY OF THE INVENTION

The present inventors found that using of an inducible system that retains the plasmid number per cell low until optimal fermentation conditions have been reached and subsequently switching the system to a high copy status minimizes the exposure of the bacterial cells to the high metabolic burden. As a result thereof, higher yields of large plasmid can be obtained and the large plasmids have a high quality.

A first aspect of the invention provides methods for the production of a vector with a size of at least 16 kb from bacterial cells which make use of a vector comprising an inducible origin of replication, whereby induction is performed when the bacterial cells reach an OD of at least 20. In particular embodiments, a method is provided for the production of a vector with a size of at least 16 kb from bacterial cells comprising the consecutive steps of a) obtaining bacterial cells comprising a vector with a size of at least 16 kb, comprising an inducible origin of replication, b) inoculating culture medium with the bacterial cells comprising the vector, c) culturing the bacterial cells in the culture medium until an optical density at 600 nm ($OD_{600}$) of at least 20 is reached, d) adding one or more inducers of said inducible origin of replication to the culture medium, e) optionally separating the bacterial cells from the culture medium, and f) recovering the plasmid from the bacterial cells.

It will be understood that cultivation of the cells is continued after step (d) to allow production of the plasmid.

More particularly, the invention the method comprises culturing the bacterial cells in the culture medium, and adding one or more inducers of said inducible origin of replication to the culture medium when the bacterial culture has reached an optical density at 600 nm ($OD_{600}$) of at least 20, after which the bacterial cells are further cultured in the culture medium. Optionally, the bacterial cells are then separated from the culture medium, and the plasmid is recovered from the bacterial cells.

In particular embodiments, the method further comprises adding an inhibitor of bacterial protein synthesis to the culture medium after the one or more inducers of said inducible origin of replication has been added, such as after step d) and before step e).

In particular embodiments, glucose and/or yeast extract are added to the culture medium during culturing the bacterial cells in the culture medium.

In particular embodiments, the culture medium comprising glucose is exchanged by culture medium comprising from 0.50% (v/v) to 2.0% (v/v) glycerol at least 30 minutes before adding the one or more inducers of plasmid replication to the culture medium.

In particular embodiments, step c) of culturing the bacterial cells in the culture medium is performed at a temperature of about 30° C. and wherein the temperature is increased from a temperature of about 30° C. to a temperature from 36.0° C. to 38.0° C. at least two hours before adding the one or more inducers of plasmid replication to the culture medium.

In particular embodiments, the inducible origin of replication comprises at least one LacO1 operator and the inducer of said inducible origin of replication is isopropyl β-D-1-thiogalactopyranoside (IPTG) and/or alpha-D-lactose.

In particular embodiments, the inhibitor of bacterial protein synthesis is chloramphenicol or spectinomycin, preferably chloramphenicol.

In particular embodiments, the inhibitor of bacterial protein synthesis is added to the culture medium at least one hour after the addition of the one or more inducers of the inducible origin of replication.

In particular embodiments, the bacterial cells are separated from the culture medium at most 6 hours after addition of the one or more inducers of the inducible origin of replication.

A further aspect provides a vector with a size of at least 16 kb comprising an inducible origin of replication.

In particular embodiments, inducible origin of replication comprises a pMB1 origin of replication:

in which the RNAI promoter is deleted or mutated such that the function of the RNAI promoter is abolished or significantly reduced, thereby obtaining a truncated RNAII pre-primer; and in which the nucleic acid sequence encoding for RNAI is deleted or mutated such that the function of RNAI is abolished or significantly reduced, thereby obtaining a truncated RNAII pre-primer; and in which at least one LacO1 operator is introduced upstream of the nucleic acid sequence encoding the truncated RNAII pre-primer, wherein the at least one LacO1 operator is operably linked to the nucleic acid sequence encoding the truncated RNAII pre-primer.

In particular embodiments, the endogenous RNAII promoter of the pMB1 origin of replication is replaced by a promoter which is not the endogenous promoter of the RNAII pre-primer of the pMB1 origin of replication and wherein said promoter which is not the endogenous promoter of the RNAII pre-primer of the pMB1 origin of replication is operably linked to the at least one LacO1 operator.

In particular embodiments, the endogenous RNAII promoter of the pMB1 ori is replaced by a promoter selected from the group consisting of the promoter of RNA I, the lac promoter, the trp promoter, the trc promoter or the T7 promoter, preferably the lac promoter, more preferably the L8/UV5 lac promoter.

A further aspect provides an inducible origin of replication comprising a pMB1 origin of replication:

in which the RNAI promoter is deleted or mutated such that the function of the RNAI promoter is abolished or significantly reduced, thereby obtaining a truncated RNAII pre-primer; and in which the nucleic acid sequence encoding for RNAI is deleted or mutated such that the function of RNAI is abolished or significantly reduced, thereby obtaining a truncated RNAII pre-primer; and in which at least one LacO1 operator is introduced upstream of the nucleic acid sequence encoding the truncated RNAII pre-primer, wherein the at least one LacO1 operator is operably linked to the nucleic acid sequence encoding the truncated RNAII pre-primer; and in which the nucleic acid corresponding to the nucleic acid at position 322 of the wild-type pMB1 origin of replication is mutated from an A to a G and/or the nucleic acid corresponding to the nucleic acid at position 543 of the wild-type pMB1 origin of replication is muted from a C to a T.

In particular embodiments, the inducible origin of replication comprises a nucleic acid sequence having at least 95%, preferably 100%, sequence identity with the nucleic sequence as set forth in SEQ ID NO 9.

In particular embodiments of the method is used for the production of a vector with a size of at least 16 kb from bacterial cells. In further embodiments said vector with a size of at least 16 kb is the vector as taught herein.

BRIEF DESCRIPTION OF DRAWINGS

FIG. 1 provides a schematic representation of the pViroVet-4-YFV17D plasmid and the iOri. oriS: ori2 replicon of the F factor: iOri: inducible origin of replication: repE: replication initiator gene; parB: partitioning protein B gene; parC: partitioning protein C gene; KanR: kanamycin resistance gene; HDrz: hepatitis virus delta ribozyme; UTR: untranslated region; YFV17D: yellow fever virus clone 17D; Lac-L8-UV: lac promoter with L8-UV5 modification; LacO1: lac operator; pMB1ori: modified origin of replication of pMB1 (ColE1).

FIG. 2 provides the nucleic acid sequences of full pMB1 (ColE1) Ori and full iOri comprising 2 point mutations in the RNAII sequence.

Ori +1—origin of DNA replication; genes in Regular letters, transcripts in Italics, proteins in Bold UPPER CASES; negative regulatory elements shaded; transcripts as wavy line with arrows indicating relative direction of transcription

Figure 3:
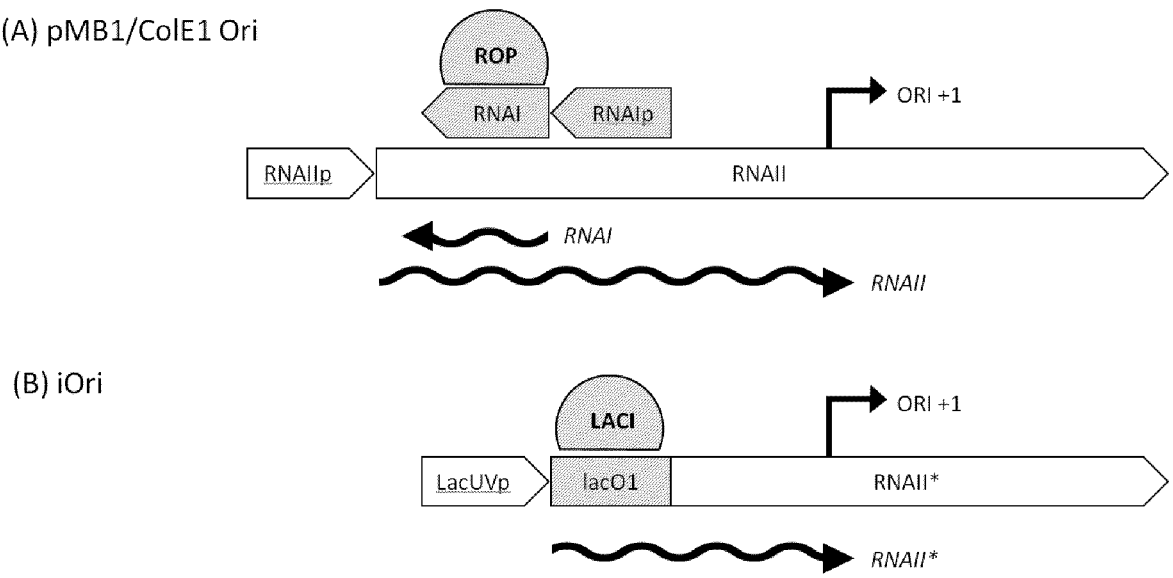
FIG. 3 (A) In the pMB1 (ColE1) Ori, the RNAII DNA is transcribed from its cognate upstream promoter RNAIIp to give rise to RNAII transcripts. RNAII serves as primer for the initiation of DNA synthesis at the Ori +1 start position of plasmid DNA. The expression of the RNAII is regulated post-transcriptionally by binding of the complementary antisense RNAI. RNAI is expressed from the RNAI gene which resides in reverse orientation within the RNAII gene, from its own RNAIp promoter. The plasmid encoded ROP protein stabilizes the RNAI-RNAII duplexes and by this means further limits plasmid DNA replication. (B) In the iOri, the expression of a 5' terminally truncated RNAII* is initiated from a heterologous LacUVp promoter. The entire RNAI gene is deleted and RNAI is not expressed. The expression of the 5' terminally truncated RNAII* (i.e. truncated RNAII pre-primer) is regulated at the transcriptional level by binding of the LACI protein to the LacO1 repressor binding sequence that is inserted between the heterologous promoter and the original, wild-type RNAII* sequence. In the iOri. RNAII* that is a transcriptional fusion of the LacO1 and the RNAII DNA sequences serves as primer for the initiation of plasmid DNA synthesis.

action (c) is increasing the temperature to 37° C. and changing glucose feed to glycerol feed; action (d) is inducing bacterial cells with IPTG; action (e) is adding chloramphenicol to the culture medium; and action (f) is harvesting the bacterial cells.

FIG. 9 shows the nucleic acid sequences represented by the SEQ ID Nos.

DETAILED DESCRIPTION OF THE INVENTION

The term "about", when used in relation to a numerical value, has the meaning generally understood in the relevant art. In certain embodiments the term "about" may be left out or may be interpreted to mean the numerical value+10%; or +5%; or +2%; or +1%.

Whenever used herein in relation to a percentage, w/w means weight/weight and w/v means weight/volume.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps. Furthermore, the terms first, second, third and the like in the description and in the claims, are used for distinguishing between similar elements or steps and not necessarily for describing a sequential or chronological order, unless specified. It is to be understood that the terms so used are interchangeable under appropriate circumstances and that the embodiments described herein are capable of operation in other sequences than described or illustrated herein.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Any references cited herein are hereby incorporated by reference.

When increasing the yield of large vectors (e.g. plasmids or bacterial artificial chromosomes (BACs)) in bacteria, there is a legitimate concern that the strongly increased activity of the replication system will increase the mutation frequency in the vector DNA. The production of large vectors thus requires a manufacturing process wherein a high yield of vector is obtained, but wherein replication of the vectors occurs without intolerable introduction of mutations.

The inventors have identified tools and methods for ensuring high yield production of large size vectors. This is of interest in the generation of vectors used e.g. in vaccination which often require large inserts. The inventors have identified that this can be ensured by making strategic use of an inducible origin of replication (ori) during cultivation of the host cells comprising said vectors. More particularly it has been found that culturing bacterial cells comprising a vector with a size of at least 16 kb comprising an inducible ori until a high culture density (e.g. an optical density at 600 nm ($OD_{600}$) of at least 20) is reached and subsequently inducing replication by adding one or more inducers of said inducible ori to the culture medium results in a large quantity of said vector. More particularly, present inventors found that by limiting the copy number of the vector per cell unit during the growth phase (e.g. at an optical density at 600 nm ($OD_{600}$) below 20) and inducing replication at a high biomass (e.g. $OD_{600}$ of at least 20) a high-quality, pharmaceutical grade vector (i.e. with low mutation frequency) can be obtained at high yield (e.g. at least 55 mg/L of vector), for example for use in DNA-based vaccines. The method for the production of a vector with a size of at least 16 kb as taught herein is scalable (e.g. up to at least 1000 L, to at least 1500 L or to at least 2000 L). Furthermore, the inventors found that a vector with a size of at least 16 kb comprising an inducible ori which comprises an inducible promoter and a nucleic acid sequence encoding for a truncated RNAII pre-primer of a ColE1-type ori, wherein the nucleic acid sequence encoding for the truncated RNAII pre-primer of a ColE1-type ori is operably linked to the inducible promoter is particularly advantageous for obtaining such high yields of vector. The inventors found that the yield can be even further increased (e.g. to at least 120 mg/L of vector) (i) by introducing a temperature shift from about 30° C. to 36-38° C. before induction: (ii) by adding inhibitors of bacterial protein synthesis after induction; and/or (iii) by adding glucose and/or yeast extract, or glycerol as a supplement to the culture medium.

Accordingly, a first aspect provides a method for the production of a vector with a size of at least 16 kb from bacterial cells comprising the consecutive steps of a) obtaining bacterial cells comprising a vector with a size of at least 16 kb, comprising an inducible ori, b) inoculating culture medium with the bacterial cells comprising the vector, c) culturing the bacterial cells in the culture medium until an optical density at 600 nm ($OD_{600}$) of at least 20 is reached, d) adding one or more inducers of said inducible ori to the culture medium, e) optionally separating the bacterial cells from the culture medium, and f) recovering the vector from the bacterial cells.

It will be understood that cultivation of the cells is continued after step (d) to allow production of the plasmid.

Accordingly, the method for the production of a vector with a size of at least 16 kb from bacterial cells can also be described as comprising the consecutive steps of obtaining bacterial cells comprising a vector with a size of at least 16 kb, comprising an inducible ori, inoculating culture medium with the bacterial cells comprising the vector.

culturing the bacterial cells in the culture medium, adding one or more inducers of said inducible ori to the culture medium when the bacterial culture has reached an optical density at 600 nm ($OD_{600}$) of at least 20, further culturing the bacterial cells in the culture medium, optionally separating the bacterial cells from the culture medium, and recovering the vector from the bacterial cells.

In particular embodiments, these steps are performed in a consecutive order.

The term "vector" as used herein refers to a circular, double-stranded DNA molecule, to which nucleic acid fragments, preferably the recombinant nucleic acid molecule as defined herein, may be inserted and cloned, i.e., propagated. Hence, a vector will typically contain one or more unique restriction sites, and may be capable of autonomous replication in a defined cell or vehicle organism such that the cloned sequence is reproducible. The skilled person will understand that for present invention, the vector is a vector capable of replicating in bacterial cells. A vector may also contain a selection marker, such as, e.g., an antibiotic resistance gene, to allow selection of recipient cells that contain the vector. Vectors may include, without limitation, plasmids, cosmids, phagemids, bacteriophage-derived vectors, PAC, BAC, etc., as appropriate. The plasmids may be plasmids intended for viral vector construction such as inter alia retroviral vectors, lentiviral vectors, adenoviral vectors, or adeno-associated viral vectors. Expression vectors are generally configured to allow for and/or effect the expression of nucleic acids or open reading frames introduced thereto in a desired expression system. e.g., in vitro, in a cell, organ and/or organism. For example, expression vectors may advantageously comprise suitable regulatory sequences.

In particular embodiments, the vector is a large vector, such as a vector with a size of at least 16 kb, at least 17 kb, at least 18 kb, at least 19 kb, at least 20 kb, at least 21 kb, or at least 22 kb, preferably at least 16 kb. "Kb", "kbp" or "kilo base pairs" as used herein refers to 1000 base pairs (bp) of DNA.

The term "bacterial cells" or "bacteria" refers to bacteria suitable as a host cell for vectors. The advantages of producing vectors in bacteria are amongst other the relatively safe and straightforward handling of bacterial cells and the rapid replication cycles of microorganisms.

In particular embodiments, for example if the inducible ori comprises a Lac O1 operator, the bacterial cells are bacterial cells comprising the Lac repressor (LacI). In more particular embodiments, the bacterial cells are cells with a sufficient amount of Lac repressor (LacI). A sufficient amount of Lac repressor is an amount of Lac repressor which prevents leakage replication of the vector within the bacterial cell in absence of the one or more inducers of the inducible ori. Preferably, the sufficient amount of Lac repressor is an amount of Lac repressor which is able to repress the replication of from 0.5 to 4 mg/L, from 0.5 to 3 mg/L, from 0.5 to 2 mg/L, or from 0.5 to 1 mg/L, of a vector in absence of the one or more inducers of the inducible ori.

In particular embodiments, the bacterial cells are *E. coli*, preferably BL21 competent *E. coli* or derivatives thereof, such as BL21 (DE3) competent *E. coli*, for example as described by F. William Studier and Barbara A. Moffatt. Use of bacteriophage T7 RNA polymerase to direct selective high-level expression of cloned genes. J. Mol. Biol. 1986 May 5; 189 (1):113-30, or DH5-alpha cells.

Bacterial cells comprising the vector with a size of at least 16 kb can be obtained by bacterial transformation as known in the art. For example, by heat shock.

The term "inducible origin of replication", "inducible ori", "iori", "conditional origin of replication" or "conditional ori" as used herein refers to a vector ori sequence that functions in a bacterial host cell and is responsive to one or more inducers of the inducible origin of replication foreign to the host cell (i.e. the bacterial cell). Preferably, the replication function of the inducible ori is severely suppressed or non-existing in absence of said one or more inducers of the inducible origin of replication. In particular embodiments, the inducible ori amplifies the vector to a high copy number in the presence of said one or more inducers of the inducible origin of replication, preferably to at least 20, at least 30, at least 40, at least 50, at least 60, at least 70, at least 80, at least 90, at least 100, at least 110, at least 120, at least 130, at least 140, at least 150, at least 200, or at least 300 copies per cell, more preferably to more than 50 copies per cell, even more preferably more than 100 copies per cell. Preferably, the inducible ori responds to a single inducer of the inducible origin of replication.

The term "inducer of the inducible origin of replication", "inducer of vector replication" or "replication-initiating agent" refers to an agent capable of inactivating (e.g. by removal) a repressor. A repressor typically inhibits or decreases the expression of one or more transcripts by binding to an operator sequence in the DNA. Binding of the repressor to the operator interferes with the binding of the RNA-polymerase to the promoter and thereby prevents transcription. An inducer of the inducible origin of replication can be capable of interfering with the binding of the repressor to the operator, thereby allowing transcription.

The skilled person will understand that the inducible ori is chosen for compatibility with a known inducer of vector replication, for its normally tight down regulation in the selected host cells in the absence of the compatible inducer of vector replication, and for its strong inducible operability in the presence of the inducer of vector replication. Non-limiting examples of inducible oris comprise the oriV/TrfA amplification system tightly controlled by the L-arabinose-inducible Para promoter (araC-PBAD)—which can be induced by the addition of L-arabinose, for example as disclosed for the amplification of a shuttle BAC vector in Wild J. et al., Conditionally amplifiable BACs: switching from single-copy to high-copy vectors and genomic clones. Genome Res. 2002.12(9):1434-1444. In a further example, the oriV/TrfA may be tightly controlled by a rhamnose-inducible Prha promoter (rhaS-Prha) as described in Wild J. et al., Copy-control tightly regulated expression vectors based on pBAC/oriV. 2004.267:155-167.

ColE1-type plasmids are known in the art and include naturally occurring plasmids (such as pMB1, pl5A, pJHCMWI) as well as many commonly used cloning vehicles (such as pBR322 and related vectors, the pUC plasmids, the pET plasmids and the pBluescript vectors). The initiation and regulation of replication of these plasmids is well known in the art. More particularly. ColE1-type plasmids replicate their DNA by using a common mechanism that involves synthesis of two RNA molecules (i.e. RNAI and RNAII) involved in regulation of replication, interaction of these RNA molecules with each other on the one hand and with the template plasmid DNA on the other hand. The ColE1 region contains two promoters, one for RNAI and one for RNAII. Replication from a ColE1-type plasmid starts with the transcription of the pre-primer RNAII, which is located 555 bp upstream of the origin of replication, by the host's RNA polymerase. During elongation, RNAII folds into specific hairpin structures and, after polymerization of about 550 nucleotides, begins to form a hybrid with the template DNA. Subsequently, the RNAII pre-primer is cleaved by RNase H to form the active RNAII primer with a free 3' OH terminus, which is accessible for DNA polymerase I. At the opposite side of the ColE1-type origin strand, RNAI, an antisense RNA of 108 nucleotides, complementary to the 5' end of RNAII, is transcribed. Transcription of RNAI starts 445 bp upstream from the replication origin and continues to approximately the starting point of RNAII transcription. RNAI inhibits primer formation, and thus replication, by binding to the elongating RNAII molecule before the RNA/DNA hybrid is formed. Apart from RNAI/RNAII interaction, the rom/rop transcript of ColE1 contributes to plasmid copy number control by increasing the rate complex formation between RNAII and RNAI. Derivatives of the ColE1-type plasmids have been developed in which the rom/rop has been deleted. Such derivatives have increased copy number. Examples of such derivatives include derivatives of pBR322, for example pUC18 and pUC19. The pUC18 and pUC19 plasmids further also comprise a single point mutation in RNAII, more particularly a G-A point mutation in nucleotide 112 of the RNA II transcript in a segment that lies immediately adjacent to the region commentary to RNA I, enhancing its ability to initiate plasmid replication.

Propagation of a plasmid in a host cell requires replication of said plasmid by the host's replication machinery. The origin of replication (ori) is a plasmid-borne DNA sequence that directs the host cell to initiate plasmid replication and is thus essential for plasmid propagation. This is accomplished by various proteins (initiators and repressors) binding to the sequence that make up the ori.

The pMB1 (ColE1) ori contains regions that promote the synthesis of RNAI and RNAII, as described above. Replication of the plasmid is typically initiated by RNAII, which is transcribed from the plasmid 550 nucleotides (nt) upstream from ori, and hybridizes strongly to the plasmid. The formation of this hybrid at the origin is a critical prerequisite for plasmid replication. The RNA part of this hybrid becomes a substrate for RNaseH, which digests away RNA II yielding a 550 nt molecule that can be used as a primer for DNA polymerase I for the initiation of replication of the entire plasmid.

The person skilled in the art will understand that the vector with a size of at least 16 kb as taught or as described herein may comprise in addition to the inducible ori an ori which makes use of different replication machinery than the inducible ori, as otherwise the two oris would compete for the same machinery, thereby creating an unstable and unpredictable environment. For example, if the inducible ori is derived from a ColE1-type ori or an ori derived thereof, the second ori can be an F1 or P1 ori or an ori derived thereof. Accordingly, in particular embodiments, the vector is a vector which is replicated by an ori different from the ColE1-type ori or an ori derived thereof (preferably pMB1 ori or an ori derived thereof), into which an inducible ori derived from a ColE-1 type ori (preferably derived from a pMB1 ori) as described herein is introduced. Non-limiting examples of vectors replicated by an ori different from a ColE-1 type ori (preferably from a pMB1 ori) include vectors comprising an F1 or P1 ori or an ori derived thereof or vectors derived thereof as known in the art. In more particular embodiments, the vector into which the inducible ori as described herein is introduced is not a ColE1-type plasmid, preferably the vector into which the inducible ori as described herein is introduced is not a pBR322 or pUC vector.

Inoculation of culture medium with the bacterial cells comprising the vector can be performed by any method known in the art to inoculate culture medium with bacterial cells. For example, a single colony of bacterial cells comprising the vector can be selected from an agar plate using a sterile pipette tip or toothpick, after which the tip or toothpick is dropped into liquid culture medium and the liquid culture medium comprising the pipette tip or toothpick is swirled. Alternatively, culture medium can be inoculated with a glycerol stock of the bacterial cells comprising the vector.

The culture medium can be any culture medium known in the art to culture bacterial cells. Non-limiting examples include Luria-Bertani Broth Medium (LB) (ATCC medium formulation 1065) or minimal medium, such as M9 minimal medium. The person skilled in the art will understand that if a minimal medium is used, supplementation with amino acids, salts and/or nutrients might be required. Use of a minimal medium offers the advantage of being able to tightly control the nutrients supplied to the bacterial cells.

In particular embodiments, the culture medium is LB medium to which at least 50 mM, at least 60 mM, at least 70 mM, at least 80 mM, or at least 90 mM phosphate is added. For example, the culture medium is LB medium to which 90 mM phosphate is added.

In particular embodiments, the culture medium is a liquid (broth) culture medium.

Biologic oxidation of carbohydrates, such as glucose, by bacteria results in synthesis of ATP as the chemical energy source and permits generation of simpler organic compounds needed by the bacteria for biosynthetic or assimilatory reactions.

Accordingly, in particular embodiments, glycerol, glucose and/or yeast extract are added to the culture medium after the step of inoculating the culture medium (step b) and before the step of culturing the bacterial cells in the culture medium (step c). In more particular embodiments, glycerol, glucose and/or yeast extract are added to the culture medium during the step of culturing the bacterial cells in the culture medium (step c).

In particular embodiments, one or more of glycerol, glucose and yeast extract (e.g. glycerol: glucose; yeast extract: glycerol and glucose: glycerol and yeast extract: glucose and yeast extract; or glycerol, glucose and yeast extract) are added to the culture medium in a total concentration of from 0.50% to 1.0% (w/v or v/v for glycerol), from 0.50% to 5.0% (w/v or v/v for glycerol), from 1.0% to 5.0% (w/V or v/v for glycerol), from 1.0% to 4.0% (w/v or v/v for glycerol), from 1.0% to 3.0% (w/v or v/v for glycerol), from 1.0% to 2.0% (w/v or v/v for glycerol), preferably from 0.50% to 2.0% (w/v or v/v for glycerol). For example, 1.0% (w/v or v/v for glycerol) one or more of glycerol, glucose and yeast extract are added are added to the culture medium.

In particular embodiments, glycerol is added to the culture medium at a concentration of from 0.50% to 5.0% (v/v), from 1.0% to 5.0% (v/v), from 1.0% to 4.0% (v/v), from 1.0% to 3.0% (v/v), or from 1.0% to 2.0% (v/v), preferably from 0.5% to 2.0% (v/v). For example, glycerol is added to the culture medium at a concentration of 1.0% (v/v).

In particular embodiments, glucose is added to the culture medium at a concentration of from 0.50% to 5.0% (w/v), from 1.0% to 5.0% (w/v), from 1.0% to 4.0% (w/v), from 1.0% to 3.0% (w/v), from 1.0% to 2.0% (w/v), preferably from 0.5% to 2.0% (w/v). For example, glucose is added to the culture medium at a concentration of 1.0% (w/v).

In particular embodiments, yeast extract is added to the culture medium at a concentration of from 0.50% to 10.0% (w/v), from 0.50% to 5.0% (w/v), from 1.0% to 5.0% (w/v), from 1.0% to 4.0% (w/v), from 1.0% to 3.0% (w/v), or from 1.0% to 2.0% (w/v).

The consumption of glycerol, glucose and/or yeast extract depends on the metabolic state of the bacterial cells. Exposing bacterial cells to a high concentration of glycerol, glucose and/or yeast extract within a short time frame could lead to osmotic lysis of the bacterial cells.

Accordingly, in particular embodiments, glucose and/or yeast extract is added continuously to the culture medium, for example by fed-batch culture, during culturing the bacterial cells in the culture medium.

In particular embodiments, glycerol is added continuously to the culture medium at a feed rate of at most 0.750% (v/v) per hour, at most 0.70% (v/v) per hour, at most 0.650% (v/v) per hour, at most 0.60% (v/v) per hour, at most 0.550% (v/v) per hour, at most 0.50% (v/v) per hour, at most 0.40% (v/v) per hour, at most 0.30% (v/v) per hour, at most 0.20% (v/v) per hour, or at most 0.10% (v/v) per hour. In particular embodiments, glucose is added to the culture medium at a feed rate of at most 0.60% (w/v) per hour, at most 0.50% (w/v) per hour, at most 0.40% (w/v) per hour, at most 0.30% (w/v) per hour, at most 0.20% (w/v) per hour, or at most 0.10% (w/v) per hour.

In particular embodiments, yeast extract is added to the culture medium at a feed rate of at most 0.30% (w/v) per hour, at most 0.20% (w/v) per hour, at most 0.10% (w/v) per hour, or at most 0.050% (w/v) per hour.

Bacterial cells especially require a source of energy during their growth phase. Therefore, in particular embodiments, one or more of glycerol, glucose and yeast extract are added to the culture medium during the growth phase of the bacterial cells.

The growth phase of bacterial cells may be determined by the optical density of the culture medium comprising the bacterial cells. The higher the concentration of bacteria in the culture medium, the higher the optical density of the culture when measured. Organic material has a high optical density at light with a wavelength of 600 nm, which allows the culture density to be measured using a spectrophotometer at a wavelength of 600 nm. The optical density of a sample of culture medium at 600 nm is referred to as "$OD_{600}$". Preferably, the sample of culture medium is undiluted. Therefore, in particular embodiments, glucose and/or yeast extract is added to the culture medium while culturing the bacterial cells in the culture medium from an optical density at 600 nm ($OD_{600}$) of 0 to 20, from 0 to 21, from 0 to 22, from 0 to 23, from 0 to 24, from 0 to 25, from 0 to 30, from 5 to 20, from 5 to 25, from 5 to 30, from 10 to 20, from 10 to 25, or from 10 to 30, preferably from 0 to 30.

Culturing of bacterial cells in culture medium can be performed by any methods known in the art for culturing of bacterial cells in culture medium. For example, liquid culture medium comprising the bacterial cells can be placed at 30° C. in a shaking incubator.

In particular embodiments, the bacterial cells are cultured at least 500 ml, at least 600 ml, at least 700 ml, at least 800 ml, at least 900 ml, at least 1000 ml, at least 1250 ml, at least 1500 ml, at least 1750 ml, at least 2000 ml, or at least 2500 ml, preferably at least 800 ml of culture medium. In more particular embodiments, the bacterial cells are cultured in from 500 to 2500 ml, from 500 to 2000 ml, from 500 to 1500 ml or from 500 to 1000 ml, preferably from 500 to 2500 ml.

Typically, the culture medium is at most 85%, preferably at most 80%, of the volume of the fermenter vessel in which the bacterial cells are cultured. Accordingly, in particular embodiments, the bacterial cells are cultured in a container with a volume from 400 ml to 2000 ml, from 400 ml to 1600 ml, from 400 ml to 1200 ml, or from 400 ml to 800 ml.

Preferably, the bacterial culture is started at a low culture density. Bacterial growth and culture density can be determined by measuring the optical density of the culture medium comprising the bacteria.

In particular embodiments, the step of culturing of the bacterial cells in culture medium is started at an optical density at 600 nm ($OD_{600}$) of at most 3, at most 2, at most 1, at most 0.5, at most 0.4, at most 0.3, at most 0.2, at most 0.1, preferably at most 0.1.

In particular embodiments, the step of culturing of the bacterial cells in culture medium is started at an optical density at 600 nm ($OD_{600}$) from 0.10 to 3.0, from 0.10 to 2.0, from 0.40 to 3.0, from 0.40 to 2.0, or from 0.50 to 2.0. For example, the bacterial cells can be diluted to a starting $OD_{600}$ of 0.1, 0.4 or 2.

The one or more inducers of said inducible origin of replication are added to the culture medium when the bacterial cell culture has reached a high culture density (e.g. $OD_{600}$ of at least 20).

Bacterial growth can be typically divided into four distinct growth phases: the lag phase, the exponential phase, the stationary phase and the death phase. The lapse of these phases provides data that can be compiled into a bacterial growth curve.

Generally, a bacterial cell culture reaches a high culture density at a late stage of the exponential phase or log (arithmic) phase of the bacterial growth curve. Accordingly, in particular embodiments, the one or more inducers of said inducible origin of replication are added to the culture medium when the number of bacterial cells is from 70 to 95%, from 75 to 95%, from 80 to 95%, from 85 to 95%, or from 85 to 90%, preferably from 85 to 90%, of the estimated maximum number of bacteria cells of the log phase of the bacterial growth curve determined for said bacterial cell culture.

The person skilled in the art will understand how to determine a bacterial growth curve for a bacteria. For example, the bacterial growth curve can be determined as described in Todar's online textbook of bacteriology http:// textbookofbacteriology.net/growth_3.html.

Similarly, in particular embodiments, the one or more inducers of said inducible origin of replication are added to the culture medium at an optical density at 600 nm ($OD_{600}$) (or when the bacterial culture or the culture medium comprising the bacterial cells has reached an $OD_{600}$) of at least 20, at least 21, at least 22, at least 23, at least 24, at least 25, at least 26, at least 27, at least 28, at least 30, at least 31, at least 32, at least 33, at least 34, at least 35, at least 36, at least 37, at least 38, at least 39, or at least 40, preferably at least 25, more preferably at least 30.

In particular embodiments, the one or more inducers of said inducible origin of replication are added to the culture medium at an optical density at 600 nm ($OD_{600}$) (or when the bacterial culture or the culture medium comprising the bacterial cells has reached an $OD_{600}$) of from 20 to 100, from 20 to 90, from 20 to 80, from 20 to 70, from 20 to 60, from 20 to 50, from 20 to 45, from 20 to 40, from 25 to 35, or from 30 to 40, preferably from 30 to 40, such as an $OD_{600}$ of 30, 31, 32, 33, 34, 35, 36, 37, 38 or 39. For example, the one or more inducers of said inducible origin of replication may be added to the culture medium at an optical density at 600 nm ($OD_{600}$) of 30.

The person skilled in the art will understand that in the present method no inducer of said inducible origin of replication is present in or added to the culture medium prior to the step of adding the one or more inducers of said inducible origin of replication to the culture medium at an optical density at 600 nm ($OD_{600}$) of at least 20 (step d).

Similarly, in particular embodiments, the one or more inducers of said inducible origin of replication are added to the culture medium from 20 to 30 hours, from 20 to 27 hours, from 23 to 27 hours or from 25 to 27 hours, such as 25, 26 or 27 hours, after the step of inoculating the culture medium with the bacterial cells comprising the vector. (step b)

In particular embodiments, the one or more inducers of the inducible origin of replication are incubated with the bacterial cells for a period of at least 1 hour, at least 2 hours, at least 3 hours, at least 4 hours, or at least 5 hours, preferably at least 2 hours, after adding said one or more inducers of the inducible origin of replication to the culture medium.

In particular embodiments, the one or more inducers of the inducible origin of replication are incubated with the bacterial cells for a period from 1 to 7 hours, from 2 to 6 hours, from 2 to 5 hours, from 2 to 4 hours, from 3 to 6 hours, or from 3 to 5 hours, preferably from 2 to 6 hours, after adding said one or more inducers of the inducible origin of replication to the culture medium.

The one or more inducers of the inducible origin of replication can be added to the culture medium by methods known in the art. For example, if the inducer of the inducible origin of replication is a chemical substance, the chemical substance can be added directly to the culture medium. In another example, if the inducer of vector replication is encoded by polynucleotide, the polynucleotide can be provided in an expression cassette under the transcriptional control of a promoter.

Glucose might interfere with the one or more inducers of plasmid replication. Accordingly, it is preferred that the glucose is removed from the culture medium and/or completely consumed by the bacterial cells before adding the one or more inducers of plasmid replication to the bacterial culture.

In particular embodiments, if the culture medium in which the bacterial cells are cultured is supplemented with glucose, the one or more inducers of plasmid replication are added to the culture medium when substantially all (e.g. at least 99.0%, preferably at least 99.90%) or all glucose present in the culture medium is consumed by the bacterial cells.

In particular embodiments, if the culture medium in which the bacterial cells are cultured is supplemented with glucose, the culture medium is exchanged by or replaced by culture medium comprising from 0.50% to 2.0% (v/v), from 0.50% to 1.50% (v/v), or from 0.50% to 1.0% (v/v) of glycerol, preferably from 0.50% to 1.0% (v/v), and comprising at most 0.010% (v/w), preferably at most 0.0010% (v/w) glucose, before addition of the one or more inducers of plasmid replication to the culture medium and/or the one or more inducers of plasmid replication are added to the culture medium when substantially all (e.g. at least 99.0%, preferably at least 99.90%) or all glucose present in the culture medium is consumed by the bacterial cells. The amount of glucose in the culture medium can be determined as known in the art, for example using high-performance liquid chromatography (HPLC) on a sample of the culture medium or the GlucCell®; Glucose Monitoring System (Cesco Bioproducts).

For certain bacterial cultures it may take at least 30 minutes for the bacterial cells to consume the glucose which remains in the bacterial cells after exchanging or replacing the culture medium which is supplemented with glucose by culture medium comprising glycerol, but no (e.g. at most 0.010% (v/w), preferably at most 0.0010% (v/w) glucose) glucose.

Similarly, in particular embodiments, if the culture medium in which the bacterial cells are cultured is supplemented with glucose, the culture medium is exchanged by or replaced by culture medium comprising from 0.50% to 2.0% (v/v), from 0.50% to 1.50% (v/v), or from 0.50% to 1.0% (v/v) of glycerol, preferably from 0.50% to 1.0% (v/v) at least 30 minutes before adding the one or more inducers of plasmid replication to the culture medium. For example, a culture medium comprising glucose and yeast extract is exchanged by or replaced by culture medium comprising 1.0% (v/v) of glycerol and yeast extract at least 30 minutes before adding the one or more inducers of plasmid replication to the culture medium. For example, if culture medium supplemented with glucose and yeast extract is added continuously to the culture medium, for example by fed-batch culture, during culturing the bacterial cells in the culture medium, the culture medium feed is switched from culture medium supplemented with glucose and yeast extract to culture medium supplemented with glycerol and yeast extract.

In particular embodiments, the culture medium comprising glucose is exchanged by or replaced by culture medium comprising from 0.50% (v/v) to 2.0% (v/v) glycerol when the culture medium comprising bacterial cells (or the bacterial culture) has an optical density at 600 nm ($OD_{600}$) from 13 to 20, from 14 to 20, from 15 to 20, from 16 to 20, from 17 to 20, from 18 to 20, from 19 to 20, from 13 to 18, from 13 to 18, preferably from 13 to 18. For example, the culture medium comprising glucose is exchanged by or replaced by culture medium comprising from 0.50% (v/v) to 2.0% (v/v) glycerol when the culture medium comprising bacterial cells (or the bacterial culture) has an optical density at 600 nm ($OD_{600}$) of 15.

In particular embodiments, for example if the culture medium in which the bacterial cells are cultured is supplemented with glucose, the culturing of the bacterial cells is performed at a temperature of about 30° C. and the temperature is increased from a temperature of about 30° C. to a temperature from 36.0° C. to 38.0° C. upon replacing the culture medium which is supplemented with glucose by culture medium comprising glycerol, but no (e.g. at most 0.010% (v/w), preferably at most 0.0010% (v/w) glucose) glucose.

In particular embodiments, the culturing of the bacterial cells is performed at a temperature of about 30° C. and the temperature is increased from a temperature of about 30° C. to a temperature from 36.0° C. to 38.0° C., at least three hours, at least two hours, at least 1.5 hours, at least one hour, at least 0.5 hour, preferably at least two hours before adding the one or more inducers of plasmid replication to the culture medium.

In particular embodiments, the temperature is increased from a temperature of about 30° C. to a temperature from 36.0° C. to 38.0° C., such as to a temperature of 36.0° C., 36.50° C., 37.0° C. 37.50° C. or 38.0° C., preferably to 37.0° C.

In particular embodiments, the temperature is increased from a temperature of about 30° C. to a temperature from 36.0° C. to 38.0° C. at an $OD_{600}$ of from 15 to 35, from 20 to 35, from 25 to 35, or from 30 to 35, before adding the one or more inducers of plasmid replication to the culture medium.

Reduced growth rate of bacteria has been linked to elevated copy numbers of plasmid. Therefore, inhibiting the bacterial protein synthesis can further elevate the yield of the method for the production of a vector with a size of at least 16 kb as taught herein.

Accordingly, in particular embodiments, the method further comprises adding one or more inhibitors of bacterial protein synthesis to the culture medium after the step of adding one or more inducers of said inducible origin of replication to the culture medium (step d) and before the optional step of separating the bacterial cells from the culture medium (step e), and before the step of recovering the plasmid from the bacterial cells (step f).

In particular embodiments, the method further comprises adding one or more inhibitors of bacterial protein synthesis to the culture medium during the further culturing of the bacterial cells in the culture medium.

The person skilled in the art will understand that no inhibitor of bacterial protein synthesis is added to the culture medium before the step of adding one or more inducers of said inducible origin of replication to the culture medium (step d).

The term "inhibitor of bacterial protein synthesis" or "bacterial protein synthesis inhibitor" as used herein refers to an agent that inhibits or slows down the growth or proliferation of bacterial cells by disrupting the processes that lead directly to the generation of polypeptides or proteins. The inhibitor of bacterial protein synthesis may suppress the bacterial internal machinery and allows the bacteria to fully focus on plasmid production. Furthermore, the inhibitor of bacterial protein synthesis may stabilize the oxygen need of the bacteria.

In particular embodiments, the one or more inhibitors of bacterial protein synthesis are added to the culture medium in a concentration from 1 mM to 10 mM, from 1 mM to 9 mM, from 1 mM to 8 mM, from 1 mM to 7 mM, from 1 mM to 6 mM, from 1 mM to 5 mM, from 1 mM to 4 mM, from 1 mM to 3 mM, or from 1 mM to 2 mM.

In particular embodiments, the one or more inhibitor of bacterial protein synthesis are agents that bind the bacterial ribosome. Non-limiting examples of such inhibitors include chloramphenicol, spectinomycin, streptomycin, aminoglycosides, tetracyclines, macrolides, lincosamides, or oxazolidinones.

In particular embodiments, the one or more inhibitor of bacterial protein synthesis are agents that inhibit peptidyl transferase activity of the bacterial ribosome. Preferably, the inhibitor of bacterial protein synthesis is an agent that binds the 50S or 30S ribosomal subunit of the bacterial ribosome. Even more preferably, the inhibitor of bacterial protein synthesis is an agent that binds amino acid residue 2451 and 2452 of the 23SrRNA of the 50S subunit of the bacterial ribosome.

In particular embodiments, the inhibitor of bacterial protein synthesis is an inhibitor of bacterial protein synthesis selected from the group consisting of chloramphenicol, spectinomycin, aminoglycosides, tetracyclines, macrolides, lincosamides, or oxazolidinones preferably chloramphenicol or spectinomycin, more preferably chloramphenicol.

In particular embodiments, the one or more inhibitors of bacterial protein synthesis are added to the culture medium when the amount of dissolved oxygen in the culture medium decreases by more than 5%, more than 10%, more than 15%, more than 20%, or more than 25%, preferably more than 5%.

In more particular embodiments, for example when the $OD_{600}$ of the bacterial culture increases by more than 10%, by more than 15% per hour, by more than 20% per hour, or by more than 25% per hour after induction, the one or more inhibitors of bacterial protein synthesis are added to the culture medium before the amount of dissolved oxygen in the culture medium is less than 40%, less than 35% or less than 30%, preferably before the amount of dissolved oxygen in the culture medium is less than 30%.

In more particular embodiments, for example when the $OD_{600}$ of the bacterial culture increases by from 1 to 10% per hour or from 5 to 10% per hour after induction, the one or more inhibitors of bacterial protein synthesis are added to the culture medium two hours before harvesting the bacterial cells.

In more particular embodiments, for example when the $OD_{600}$ of the bacterial culture increases by from 10 to 25% per hour after induction and when the dissolved oxygen in the culture medium is more than 35% or more than 30%, the one or more inhibitors of bacterial protein synthesis is added to the culture medium two hours before harvesting the bacterial cells.

In particular embodiments, the one or more inhibitors of bacterial protein synthesis are incubated with the bacterial cells for a period of at least 1 hour, at least 2 hours, or at least 3 hours, preferably at least 1 hour, after adding said one or more inhibitors of bacterial protein synthesis to the culture medium.

In particular embodiments, the one or more inhibitors of bacterial protein synthesis are incubated with the bacterial cells for a period from 1 to 5 hours, from 1 to 4 hours, from 1 to 3 hours, from 2 to 3 hours, or from 1 to 2 hours, preferably from 1 to 4 hours, after adding said one or more inhibitors of bacterial protein synthesis to the culture medium.

In particular embodiments, the one or more inhibitors of bacterial protein synthesis are added to the culture medium at least one hour after the addition of the one or more inducers of the inducible origin of replication.

The skilled person will understand that in order to prevent the bacteria from producing vector of less quality, the bacterial cells need to be harvested prior to exhaustion of RNA polymerase in the bacteria and/or prior to the dissolved oxygen has reached a concentration of less than 40%, less than 35% or less than 30%, preferably less than 30%. Preferably, the pH of the culture medium is between 6.5 and 7.5, preferably between 6.9 and 7.1.

Accordingly, in particular embodiments, the bacterial cells are cultured further (in step e) for at most 4 hours, at most 5 hours, at most 6 hours, at most 7 hours, at most 8 hours, preferably at most 6 hours, such as 6, 5, 4, 3, 2 or 1 hour. In particular embodiments, the bacterial cells are separated from the culture medium at most 4 hours, at most 5 hours, at most 6 hours, at most 7 hours, at most 8 hours, preferably at most 6 hours, such as 6, 5, 4, 3, 2 or 1 hour, after the addition of the one or more inducers of the inducible origin of replication.

In particular embodiments, the bacterial cells are separated from the culture medium before the dissolved oxygen in the culture medium has reached a concentration of less than 40%, less than 35% or less than 30%, preferably less than 30%.

In particular embodiments, the bacterial cells are separated from the culture medium when the optical density at 600 nm ($OD_{600}$) of the bacterial culture decreases, preferably when the $OD_{600}$ of the bacterial culture decreases by from 1 to 20%, from 1 to 15%, from 1 to 10%, or from 5 to 10%.

The bacterial cells can be separated from the culture medium by any method known in the art to separate cells from culture medium. For example, the culture medium comprising the bacterial cells can be centrifuged and the pellet can be collected.

The vector can be recovered from the bacterial cells or bacterial milieu by any method known in the art to recover vectors from bacteria. For example, by first lysing the bacterial cells such as by using a lysis buffer (e.g. a buffer comprising alkaline) and/or sonication, and subsequently purifying the vector DNA, such as by ethanol precipitation, spin column-based nucleic acid purification or phenol-chloroform extraction. The purified vector DNA can be extracted extensively with phenol, chloroform, and ether, to ensure that no bacterial proteins are present in the plasmid DNA preparation, since these proteins can be toxic to mammalian cells.

The presence of an inducible origin of replication in the vector allows to induce transcription within the cell and, hence, control the switch from low to high copy number, at any time point of interest during the bacterial culture.

Inducible origins of replication and their compatible inducers are well known in the art.

An origin of replication may be rendered inducible by operably linking an inducible promoter/repressor system to the origin of replication.

For example, the inducible origin of replication may be the oriV/TrfA amplification system tightly controlled by the 1-arabinose-inducible Para promoter (araC-PBAD); which can be induced by the addition of 1-arabinose, for example as disclosed for the amplification of a shuttle BAC vector in Wild J. et al., Conditionally amplifiable BACs: switching from single-copy to high-copy vectors and genomic clones. Genome Res. 2002.12 (9): 1434-1444. In a further example, the inducible origin of replication may be tightly controlled by a rhamnose-inducible Prha promoter (rhaS-Prha) as described in Wild J. et al., Copy-control tightly regulated expression vectors based on pBAC/oriV. 2004.267:155-167.

In preferred embodiments, said inducible origin of replication comprises, consists essentially of or consists of:

an inducible promoter (i.e. inducible promoter/repressor system); preferably wherein the inducible promoter comprises, consists essentially of, or consists of a lac promoter and at least one LacO1 operator, wherein the at least one LacO1 operator is operably linked to the lac promoter; and a nucleic acid sequence encoding for a truncated RNAII pre-primer of a ColE1-type origin of replication, wherein the nucleic acid sequence encoding for the truncated RNAII pre-primer of a ColE1-type origin of replication is operably linked to the inducible promoter: preferably operably linked to the Lac promoter and the LacO1 operator, as described elsewhere herein.

In particular embodiments, the method as taught herein allows controlling the copy number of the vector in said bacterial cells.

In particular embodiments, the method as taught herein reduces the mutation rate and/or the number of undesired mutations in the obtained vectors. The mutation rate in a bacterial population may be determined by methods known in the art, such as described in Rosche et al., Determining mutation rates in bacterial populations. Methods. 2000, 20 (1): 4-17.

Present inventors have developed a large vector comprising an inducible ori which results in a particularly high plasmid production when the vector is produced by the method as taught herein. Furthermore, present inventors have developed an improved inducible ori which results in an ever higher plasmid production than by the large vector comprising the wild-type inducible ori.

Accordingly, a further aspect provides a vector of at least 16 kb comprising an inducible origin of replication.

In particular embodiments, said inducible ori comprises, consists essentially of or consists of:

an inducible promoter (i.e. promoter/repressor system); preferably wherein the inducible promoter comprises, consists essentially of, or consists of a lac promoter and at least one LacO1 operator, wherein the at least one LacO1 operator is operably linked to the lac promoter; and a nucleic acid sequence encoding for a truncated RNAII pre-primer of a ColE1-type ori, wherein the nucleic acid sequence encoding for the truncated RNAII pre-primer of a ColE1-type ori is operably linked to the inducible promoter, preferably to the LacO1 operator and the Lac promoter.

An "operable linkage" is a linkage in which regulatory sequences and sequences sought to be transcribed or expressed are connected in such a way as to permit said transcription or expression. For example, sequences, such as, e.g., a promoter and an ORF, may be said to be operably linked if the nature of the linkage between said sequences does not: (1) result in the introduction of a frame-shift mutation. (2) interfere with the ability of the promoter to direct the transcription of the ORF. (3) interfere with the ability of the ORF to be transcribed from the promoter sequence. Hence. "operably linked" may mean incorporated into a genetic construct so that expression control sequences, such as a promoter, effectively control transcription/expression of a sequence of interest.

The term "wild-type RNAII pre-primer" as used herein refers generally to a nucleic acid sequence comprising a sequence encoding RNAII, the antisense RNAI promoter and an antisense sequence encoding RNAI.

The term "truncated RNAII pre-primer" as used herein refers generally to the fact that there is no sequence present which encodes a functional RNAI, i.e. no sequence which is capable of interacting with RNAII and/or no sequence present which encodes a functional RNAI promoter operably linked to the sequence encoding for RNAI. RNAI is a counter-transcript to a section of RNAII. Typically, removal of the sequence encoding RNAI and/or the RNAI promoter implies that the RNAII pre-primer sequence is shorter than the wild-type RNAII pre-primer sequence containing the RNA I sequence and/or the RNA I promoter. However, as also described further herein, it will be clear to the skilled person that deletion of parts of the RNAI encoding sequence and/or mutations in said sequence will also result in a non-functional RNAI sequence. Similarly, it will be clear to the skilled person that deletion of parts of the RNAI promoter and/or mutations in said sequence will also result in a non-functional RNAI promoter. For example, the truncated RNAII pre-primer can comprise, consist essentially of or consist of a sequence as set forth in SEQ ID NO 6 or 7.

Accordingly, in particular embodiments, said inducible origin of replication does not comprise a nucleic acid sequence encoding for a functional (i.e. capable of interacting with RNAII) RNAI of a ColE1-type ori, preferably said inducible origin of replication does not comprise a nucleic acid sequence encoding for a functional (i.e. capable of interacting with RNAII) RNAI of the pMB1 (ColE1) ori.

In more particular embodiments, said inducible ori does not comprise a nucleic acid sequence as set forth in SEQ ID NO 1.

In particular embodiments, said inducible ori does not comprise a functional RNAI promoter of a ColE1-type ori, preferably said inducible ori does not comprise a functional RNAI promoter of the pMB1 (ColE1) ori. In more particular embodiments, said inducible ori does not comprise a nucleic acid sequence as set forth in SEQ ID NO 2.

In particular embodiments, said inducible ori and/or said inducible promoter does not comprise the endogenous promoter of the RNAII pre-primer. In more particular embodiments, said inducible ori and/or said inducible promoter does not comprise the endogenous promoter of the RNAII pre-primer of the pMB1 ori. In even more particular embodiments, said inducible ori and/or said inducible promoter/repressor system does not comprise a nucleic acid sequence as set forth in SEQ ID NO 3.

In particular embodiments, the vector does not comprise the rop gene or comprises a rop gene encoding for an inactive rop.

As used herein, the term "promoter" refers to a DNA sequence that enables a gene to be transcribed. A promoter is recognized by RNA polymerase, which then initiates transcription. Thus, a promoter contains a DNA sequence that is either bound directly by, or is involved in the recruitment, of RNA polymerase. A promoter sequence can also include "enhancer regions", which are one or more regions of DNA that can be bound with proteins (namely the trans-acting factors) to enhance transcription levels of genes in a gene-cluster. The enhancer, while typically at the 5' end of a coding region, can also be separate from a promoter sequence, e.g., can be within an intronic region of a gene or 3' to the coding region of the gene. When reference is made herein to an "inducible promoter", an inducible promoter/repressor system is intended comprising a promoter region and an operator region to which one or more regulatory proteins (repressor and/or activator) can bind (i.e. the operator). Binding of the one or more regulatory proteins to the operator region can increase or reduce the affinity of the promoter to the RNA polymerase. When reference is made herein to a "promoter", a promoter per se is intended, i.e. without the operator region.

In particular embodiments, the inducible promoter comprises a promoter selected from the group consisting of the promoter of RNA I, the lac promoter, the trp promoter, the trc promoter or the T7 promoter, preferably the lac promoter.

In particular embodiments, the lac promoter is the wild type lac promoter or a modified lac promoter. In more particular embodiments, the lac promotor contains the lacL8 promoter, also known as the lacUV5 promoter or L8-UV5 lac promoter. The lacL8promoter comprises 2 base pair mutations in the −10 hexamer region, compared to the wild type lac promoter. The lacL8promoter is previously described in Magasanik, The lactose operon, Cold Spring Harbour Laboratory Press, Cold Spring Harbour, NY, 1972.

In particular embodiments, the lac promoter comprises, consists essentially of or consists of a nucleic acid sequence having at least 70%, at least 75%, at least 80%, at least 85%, at least 90%, at least 95%, or at least 99%, preferably 100%, sequence identity with the nucleic sequence as set forth in SEQ ID NO 4.

The person skilled in the art will understand that the final transcription start is determined by the promoter which is present in the inducible ori.

In particular embodiments, the inducible promoter comprises at least one (such as one, two or three) LacO1 operator. The use of multiple LacO1 operators upstream of the nucleic acid sequence encoding for a truncated RNAII pre-primer could result in a tighter control of the replication of the vector.

In particular embodiments, the LacO1 operator comprises, consists essentially of or consists of a nucleic acid sequence having at least 70%, at least 75%, at least 80%, at least 85%, at least 90%, at least 95%, or at least 99%, preferably 100%, sequence identity with the nucleic sequence as set forth in SEQ ID NO 5.

In particular embodiments, the nucleic acid sequence encoding for the truncated RNAII pre-primer of a ColE1-type origin of replication encodes for a truncated RNAII pre-primer of the pMB1 (ColE1) origin of replication.

The person skilled in the art will understand that, as RNAI is a counter-transcript to a section of RNAII, the nucleic acid sequence encoding for RNAII of the ColE1-type ori will be truncated in such a way as to not comprise the counter-transcript encoding for RNAI of the ColE1-type ori. Furthermore, the nucleic acid sequence encoding for RNAII of the ColE1-type ori can further also be truncated in such a way as to not comprise the antisense RNAI promoter of the ColE1-type ori. The truncated RNAII pre-primer will abolish or at least reduce the negative RNAI-RNAII duplexing feedback loop.

In particular embodiments, the nucleic acid sequence encoding for the truncated RNAII pre-primer of the pMB1 (ColE1) origin of replication comprises, consists essentially of or consists of a nucleic acid sequence having at least 70%, at least 75%, at least 80%, at least 85%, at least 90%, at least 95%, or at least 99%, preferably 100%, sequence identity with the nucleic sequence as set forth in SEQ ID NO 6. Preferably, the nucleic acid sequence encoding the truncated RNAII pre-primer has a nucleic acid sequence comprises or consists of a nucleic acid sequence as set forth in SEQ ID NO 6.

Present inventors found that the presence of two mutations in the truncated RNAII pre-primer increases vector production compared to the wild-type truncated pMB1 origin of replication.

In particular embodiments, the truncated RNAII pre-primer comprises a C to T point mutation at a nucleic acid position which corresponds to nucleic acid 543 of the full RNA II pre-primer transcript (i.e. before truncation) and/or an A to G point mutation at a nucleic acid position which corresponds to nucleic acid 322 of the full RNA II pre-primer transcript (i.e. before truncation). In particular embodiments, the truncated RNAII pre-primer comprises a C to T point mutation at a nucleic acid position which corresponds to nucleic acid 543 of SEQ ID NO 10 and/or an A to G point mutation at a nucleic acid position which corresponds to nucleic acid 322 of SEQ ID NO 10.

In particular embodiments, the truncated RNAII pre-primer comprises a C-T point mutation in nucleic acid 306 of the truncated RNA II transcript and/or a A-G point mutation in nucleic acid 85 of the truncated RNA II transcript.

In particular embodiments, the nucleic acid sequence encoding the truncated RNAII pre-primer comprises or consists of a nucleic acid sequence having at least 70%, at least 75%, at least 80%, at least 85%, at least 90%, at least 95%, or at least 99%, preferably 100%, sequence identity with SEQ ID NO 7. Preferably, the nucleic acid sequence encoding the truncated RNAII pre-primer has a nucleic acid sequence comprises or consists of a nucleic acid sequence as set forth in SEQ ID NO 7. The inducible ori as disclosed herein may be derived from a plasmid comprising a pMB1 (ColE1-type) ori, such as a pUC18 plasmid, by (i) deleting the nucleic acid sequence encoding for RNAI from the pMB1 ori or mutating the nucleic acid sequence encoding for RNAI in the pMB1 ori such that the function of the RNAI is abolished or significantly reduced:

(ii) deleting the RNAI promoter from the pMB1 ori or mutating the RNAI promoter in the pMB1 ori such that the function of the RNAI promoter is abolished or significantly reduced:

(iii) optionally replacing the RNAII promoter of the pMB1 ori by a promoter which is not the endogenous promoter of the RNAII pre-primer of the pMB1 ori, preferably wherein the promoter which is not the endogenous promoter of the RNAII pre-primer of the pMB1 ori is a promoter selected from the group consisting of the RNA I promoter, the lac promoter, the trp promoter, the trc promoter or the T7 promoter, more preferably wherein the promoter which is not the endogenous promoter of the RNAII pre-primer of the pMB1 ori is the lac promoter: wherein the promoter which is not the endogenous promoter of the RNAII pre-primer of the pMB1 ori is operably linked to the nucleic acid sequence encoding the truncated RNAII pre-primer; and (iv) introducing at least one (such as one, two, three or more) operator upstream (5') of the nucleic acid sequence encoding the truncated RNAII pre-primer, wherein the at least one operator is operably linked to the nucleic acid sequence encoding the truncated RNAII pre-primer and wherein the operator allows in combination with the endogenous RNAII promoter or the optional replacement promoter of said endogenous RNAII promoter conditional transcription of said truncated RNAII pre-primer.

As described above, as RNAI is a counter-transcript to a section of RNAII, deleting from the pMB1 ori the nucleic acid sequence encoding for RNAI will result in a nucleic acid sequence encoding for a truncated RNAII pre-primer.

In more particular embodiments, the inducible origin of replication as disclosed herein may be derived from the pMB1 ori by altering the pMB1 ori as described in European patent EP0179786 B1, which is incorporated herein by reference, and Panayotatos et al., DNA replication regulated by the priming promoter, Nucleic Acids Research, 1984, Volume 12 (8): 2641-2648.

In particular embodiments, said inducible origin of replication is a pMB1 origin of replication:

in which the RNAI promoter is deleted or mutated such that the function of the RNAI promoter is abolished or significantly reduced; thereby obtaining a truncated RNAII pre-primer;

in which mutations are introduced in the nucleic acid sequences of the RNAI/RNAII overlap that decrease the affinity of the RNAI/RNAII interaction: preferably in which the nucleic acid sequence encoding for RNAI is deleted or mutated such that the function of the RNAI is abolished or significantly reduced: thereby obtaining a truncated RNAII pre-primer;

in which at least one (such as one, two, three or more) operator is introduced upstream (5') of the nucleic acid sequence encoding the truncated RNAII pre-primer, wherein the at least one operator is operably linked to the nucleic acid sequence encoding the truncated RNAII pre-primer and wherein the at least one operator allows in combination with the endogenous RNAII promoter or the optional replacement promoter of said endogenous RNAII promoter conditional transcription of said truncated RNAII pre-primer; and/or in which, optionally, the RNAII promoter is replaced by a promoter which is not the endogenous promoter of the RNAII pre-primer, preferably in which the RNAII promoter is replaced by a promoter selected from the group consisting of the RNA I promoter, the lac promoter, the trp promoter, the trc promoter or the T7 promoter: wherein the promoter which is not the endogenous promoter of the RNAII pre-primer is operably linked to the nucleic acid sequence encoding the truncated RNAII pre-primer.

Mutations in the area of RNAI/RNAII overlap that decrease the affinity of the RNAI/RNAII interaction are known in the art and are described in, for example, Table 2 of Camps et al., Modulation of ColE1-like plasmid replication for recombinant gene expression. Recent Pat DNA Gene Seq. 2010, 4 (1): 58-73.

In preferred embodiments, said inducible origin of replication is a pMB1 origin of replication:

from which the nucleic acid sequence encoding for RNAI gene and the RNAI promoter are deleted:

in which at least one (such as one, two, three or more) LacO1 operator is introduced upstream (5') of the nucleic acid sequence encoding the RNAII pre-primer, wherein the at least one LacO1 operator is operably linked to the nucleic acid sequence encoding the (truncated) RNAII pre-primer; and in which the RNAII promoter is replaced a promoter which is not the endogenous promoter of the RNAII pre-primer, preferably in which the RNAII promoter is replaced by a promoter selected from the group consisting of the RNA I promoter, the lac promoter, the trp promoter, the trc promoter or the T7 promoter: wherein the promoter which is not the endogenous promoter of the RNAII pre-primer is operably linked to the nucleic acid sequence encoding the truncated RNAII pre-primer.

In particular embodiments, the inducible origin of replication comprises, consists essentially of or consists of the sequence of SEQ ID NO 8.

As described above, present inventors found that the introduction of one or two mutations into the truncated pMB1 origin of replication increased vector production compared to the wild-type truncated pMB1 origin of replication.

Accordingly, in particular embodiments, the inducible ori comprises an A to G mutation at nucleic acid position 176 of the amino acid sequence as set forth in SEQ ID NO: 8 and/or a C to T mutation at nucleic acid position 397 of the amino acid sequence as set forth in SEQ ID NO: 8.

In preferred embodiments, the inducible origin of replication comprises, consists essentially of or consists of a sequence as set having at least 70%, at least 75%, at least 80%, at least 85%, at least 90%, at least 95%, or at least 99%, preferably 100%, sequence identity with SEQ ID NO 9. The skilled person will understand that the sequence as set forth in SEQ ID NO 9 may comprise mutations in addition to these at nucleic acid position 176 and/or nucleic acid position 397.

In particular embodiments, if the inducible origin of replication as described herein comprises a LacO1 operator operably linked to a lac promoter, the inducer is isopropyl β-D-1-thiogalactopyranoside (IPTG) and/or alpha-D-lactose. IPTG will remove the endogenous repressor LacI from the LacO1 operator and the inducible origin of replication will then overrule any other origin of replication present in the plasmid.

The person skilled in the art will understand that the vector of at least 16 kb as taught herein may further comprise other factors required for vector replication, cell division and/or selection, including, but not limited thereto:

repE for plasmid replication and regulation of the copy number, parA and parB for partitioning F plasmid DNA to daughter cells during division and/or ensuring stable maintenance of the vector; and/or a selection marker, such as an antibiotic resistance gene or an antibiotic-independent selection marker (e.g. Ccda/ccdb poison/anti-poison system (The Staby® Operating System: Delphi Genetics) or metabolic dependency).

In particular embodiments, the empty backbone vector into which the inducible ori as described herein is cloned is the pShuttle vector and/or a BAC vector, or combinations thereof. For example, the pShuttle vector of Addgene with product number #16402.

The vector of present invention may be used in next-generation vaccine platform technology, such as a plasmid launched live attenuated virus (PPLAV) vaccine. Accordingly, in particular embodiments, the vector comprises a viral expression cassette comprising the cDNA of a life-attenuated (flavi)virus vaccine. In more particular embodiments, the vector comprises a viral expression cassette comprising the cDNA of a life-attenuated yellow fever virus (YFV)-17D vaccine, wherein heterologous DNA sequences have been inserted and/or native viral sequences have been deleted.

A further aspect provides use of the vector as taught herein for vaccination, for manufacturing large polypeptides or proteins, or for the production of viral vectors. The following examples are meant to illustrate the present invention and should not be construed as a limitation of its scope.

EXAMPLES

Example 1: Comparison of pMB1 (ColE1) Ori with iOri

In the pMB1 (ColE1) Ori (see SEQ ID NO 10), the RNAII DNA is transcribed from its cognate upstream promoter RNAIIp to give rise to RNAII transcripts. RNAII serves as primer for the initiation of DNA synthesis at the Ori +1 start position of plasmid DNA. The expression of the RNAII is regulated post-transcriptionally by binding of the complementary antisense RNAI. RNAI is expressed from the RNAI gene which resides in reverse orientation within the RNAII gene, from its own RNAIp promoter. The plasmid encoded ROP protein stabilizes the RNAI-RNAII duplexes and by this means further limits plasmid DNA replication (FIGS. 2-3).

In the iOri, the expression of a 5' terminally truncated RNAII* is initiated from a heterologous LacUVp promoter. The RNAII sequence is truncated by deleting the entire RNAI gene and RNAI is not expressed. The expression of RNAII* is regulated at the transcriptional level by binding of the LACI protein to the LacO1 repressor binding sequence that is inserted between the heterologous promoter and the original RNAII* sequence. In the iOri. RNAII* that is a transcriptional fusion of the LacO1 and the RNAII DNA sequences serves as primer for the initiation of plasmid DNA synthesis. The RNAII* may comprise two point mutations. C→T at nucleic acid location 397 and one A→G at nucleic acid location 176 (see SEQ ID NO 9) (FIGS. 2-3).

Example 2: Effect of Point Mutations in RNAII* of iOri on Plasmid Production A plasmid with a structure as illustrated in FIG. 1 (pViroVet-4-YFV17D with a mutated iOri) or a plasmid with a structure as illustrated in FIG. 1 in which the mutated iOri is replaced by a wildtype iOri (i.e. the iOri as shown in FIG. 2 without the point mutations C→T at nucleic acid location 397 and A→G at nucleic acid location 176) (unmutated iOri) was used to transform BL21 bacteria.

Phosphate buffered LB medium was inoculated with two different bacterial clones transformed with pViro Vet-4-YFV17D with a mutated iOri (pVV* and pVV4) and one bacterial clone transformed with a pViro Vet-4-YFV17D with iOri which is not mutated (pVV-wt iOri) and incubated overnight in a shaker flask.

The next morning the $OD_{600}$ of the bacterial culture was measured, and the bacteria were diluted to an $OD_{600}$ of 2 in fresh medium supplemented with 1% glycerol in the fermenter vessel. The bacteria were grown at 37° C. for two hours before being induced with IPTG. Two hours post induction, chloramphenicol was added to a) suppress the bacterial internal machinery and focusing fully on the plasmid production and b) to stabilize the oxygen need of the bacteria. Two hours after addition of chloramphenicol, the cells were harvested, and the yield was measured.

Figure 5:
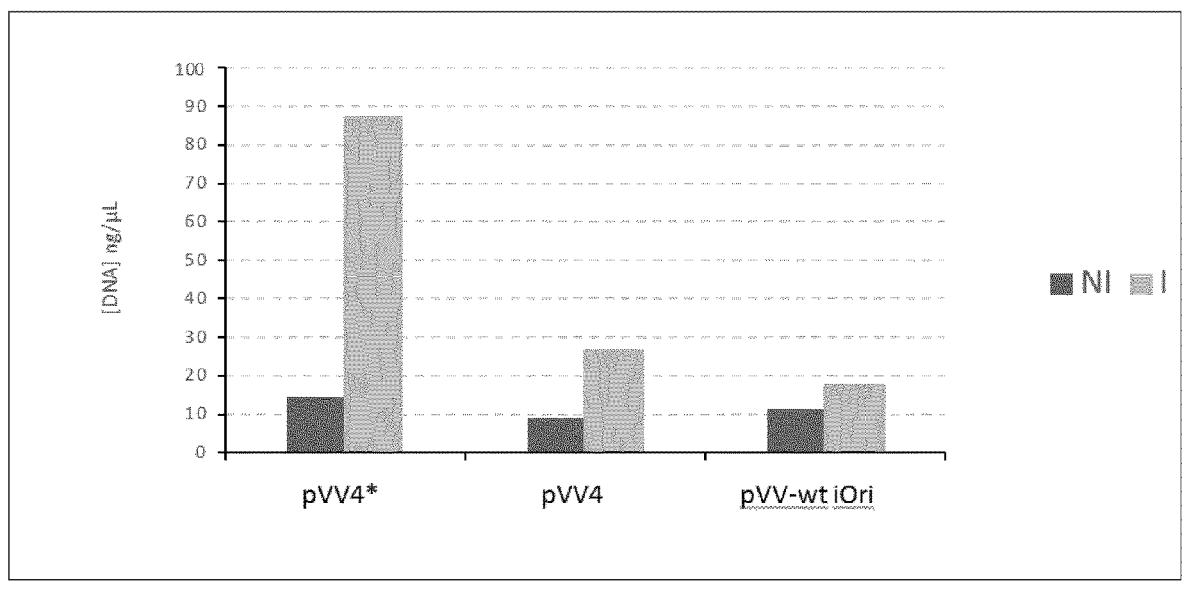
FIG. 5 shows the beneficial effect on vector production of the mutated iOri compared to wild-type iOri. pVV4* refers to a first clone of the pViro Vet-4-YFV17D plasmid shown in FIG. 1, pVV4 refers to a second clone of the pViroVet-4-YFV17D plasmid shown in FIG. 1, pVV-wt iOri refers to the pViro Vet-4-YFV17D plasmid in which the mutated iOri is replaced by a wild-type (i.e. not mutated) iOri, NI, not induced; I, induced.

FIG. 5 shows that induction (I) of bacterial clones pVV4* or pVV4 resulted in a higher plasmid production as compared to induction of bacterial clone pVV-wt iOri. Accordingly, the mutations point mutations C→T at nucleic acid location 397 of the iOri and A→G at nucleic acid location 176 of the iOri have a beneficial effect on plasmid production.

Example 3: Effect of the Level of Biomass at Time of Induction of Replication on the Yield of a Vector as Taught Herein A plasmid with a structure as illustrated in FIG. 1 (pViroVet-4-YFV17D) and comprising iOri was used to transform BL21 bacteria and a glycerol stock was prepared using state of the art techniques, for example as described in the Transformation Protocol for BL21 (DE3) competent cells of New England BioLabs Inc. on https://international.neb.com/Protocols/0001/01/01/transformation-protocol-for-b121-de3-competent-cells-c2527 and as described in the protocol for creating bacterial glycerol stocks for long-term storage of plasmids on the addgene homepage https://www.addgene.org/protocols/create-glycerol-stock/.

Table 1 shows the effect of the level of biomass at time of induction of replication on the yield of a plasmid of this invention.

| $OD_{600}$ at seeding | $OD_{600}$ at induction | $OD_{600}$ harvest | yield mg/l |
|---|---|---|---|
| 0.1 | 1 | 2.57 | 0.40 |
| 0.4 | 2 | 4.41 | 0.98 |

-continued

| OD$_{600}$ at seeding | OD$_{600}$ at induction | OD$_{600}$ harvest | yield mg/l |
|---|---|---|---|
| 2 | 3.78 | 5.88 | 0.92 |
| ON incubation | 10 | 12.00 | 1.28 |
| ON incubation in fermenter | 33 | 38 | 46 |

Abbreviations: ON: overnight

LB medium was inoculated with a glycerol stock of bacteria transformed with pViro Vet-4-YFV17D (FIG. 1) and incubated overnight in a shaker flask. The next morning the biomass, reflected by OD$_{600}$ values, was measured, and the bacteria were diluted to the starting OD$_{600}$ of 0.1, 0.4, and 2. One culture was seeded at OD$_{600}$ 0.2 and incubated for another overnight to reach an OD$_{600}$ of 10 at induction. After the bacterial density reached 1, 2, 3.78 and 10, the cultures were given 1 mM IPTG to induce plasmid replication. Cells were harvested 2 hours after induction to determine the yield (expressed as mg/l) of the plasmid production. More particularly, cells were lysed by addition of alkaline, after which the mixture was neutralized and cell debris was removed by tangential flow filtration. Next, ion exchange chromatography, ultra filtration and tangential flow filtration (for possible buffer exchange), followed by a final polishing column were used to isolate and purify the plasmid.

Temperature was kept at 37° C. at all times.

The yield increased with increasing biomass at induction including a fermenter run which achieved much higher biomass compared to the limitations of a shaker flask (see Table 1). It was concluded, that the higher the bacterial biomass, the higher the yield of plasmid production.

Example 4: The Vector as Taught Herein Comprising iOri can be Induced with Both IPTG and Alpha-D-Lactose Medium was inoculated with a glycerol stock of bacteria transformed with pViro Vet-4-YFV17D (FIG. 1) and incubated overnight in a shaker flask. The next morning the OD$_{600}$ was measured, and the bacteria were diluted to an OD$_{600}$ of 2 and further grown for 2 hours. One cell culture was then allowed to grow in the absence of a plasmid inducer (NI=non-induced), whereas the other cultures were either induced with 1 mM IPTG or increasing amounts of alpha-D-lactose (i.e. 0.5, 1, 2, and 5%). All cultures were harvested after 4 hours, the DNA was isolated, digested by restriction enzymes, applied on a gel and visualized. Temperature was kept at 37° C. at all times.

Figure 4:
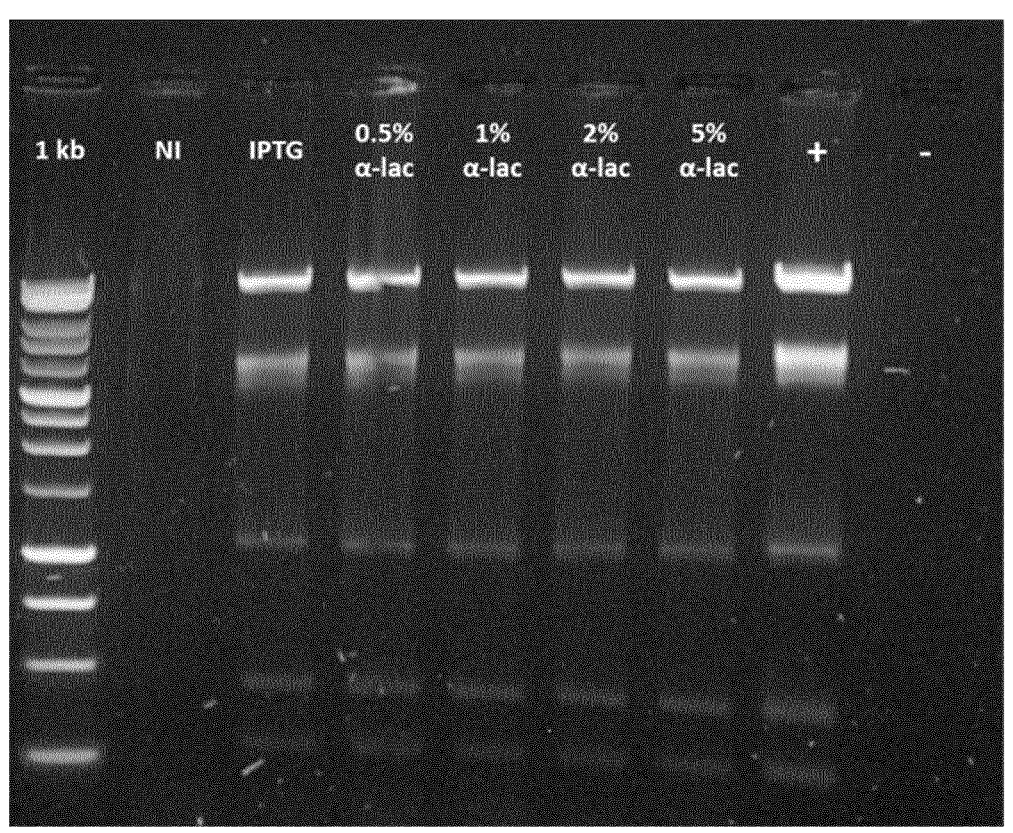
FIG. 4 shows the inducibility of the plasmid as taught herein with both IPTG and alpha-D-lactose.

All cultures that were induced showed presence of the plasmid with no obvious difference between the IPTG and the different concentrations of alpha-D-lactose (FIG. 4). It was concluded that the plasmid can be induced with both IPTG and alpha-D-lactose.

Example 5. Addition of Glycerol or Glucose to the Culture Medium Increased the Bacterial Growth Medium was inoculated with a glycerol stock of bacteria transformed with pViro Vet-4-YFV17D (FIG. 1) and incubated overnight in a shaker flask. The next morning the OD$_{600}$ was measured, and the bacteria were diluted to an OD$_{600}$ of 0.1 in fresh medium supplemented with either 1% glycerol. 1% glucose or not supplemented. Cells were grown for 8 hours and OD$_{600}$ was measured every hour. Cells were not induced. Temperature was kept at 37° C. at all times.

Figure 6:
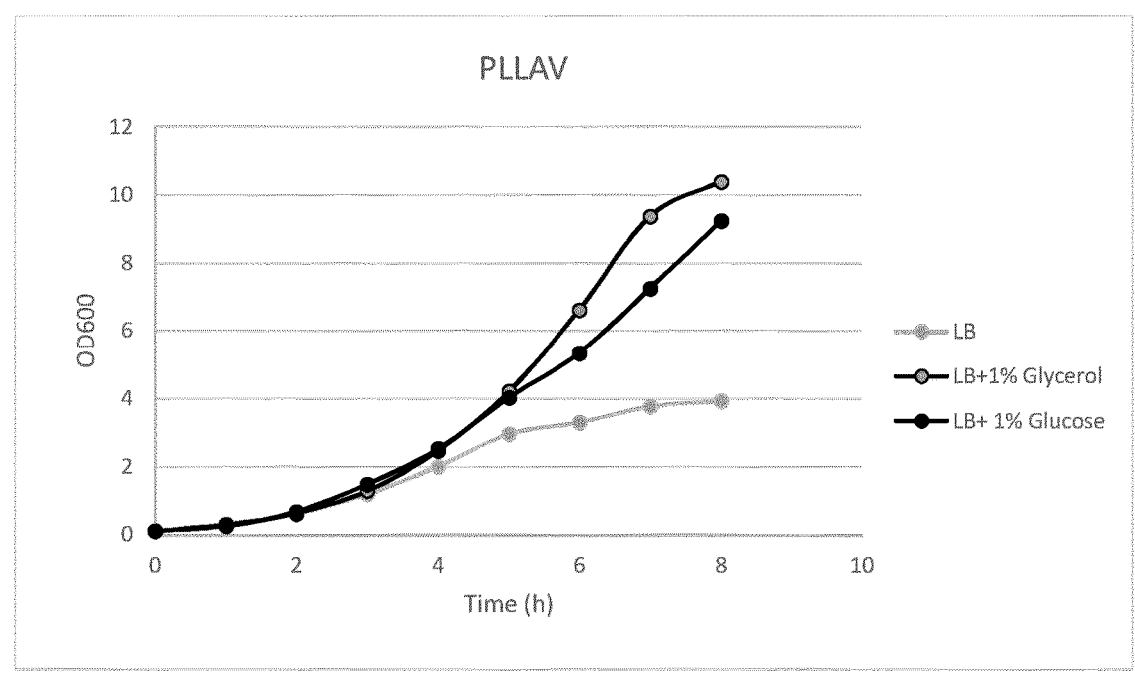
FIG. 6 represents the beneficial effect on vector production of adding glucose or glycerol as a supplement to the feed.

Addition of glycerol or glucose increased the bacterial growth by 2-2.5-fold (FIG. 6).

Example 6. Addition of Inhibitor of Bacterial Protein Synthesis Chloramphenicol is Beneficial for the Plasmid Production Medium was inoculated with a glycerol stock of bacteria transformed with pViro Vet-4-YFV17D (FIG. 1) and incubated overnight in a shaker flask at 37° C. The next morning the OD$_{600}$ was measured, and the bacteria were diluted to an OD$_{600}$ of 0.1 in fresh medium supplemented with glucose in the fermenter vessel and incubated overnight at 37° C. (FIG. 7, action (a): seeding). In the morning, the feed was supplemented with glycerol (FIG. 7, action (b)).

Figure 7:
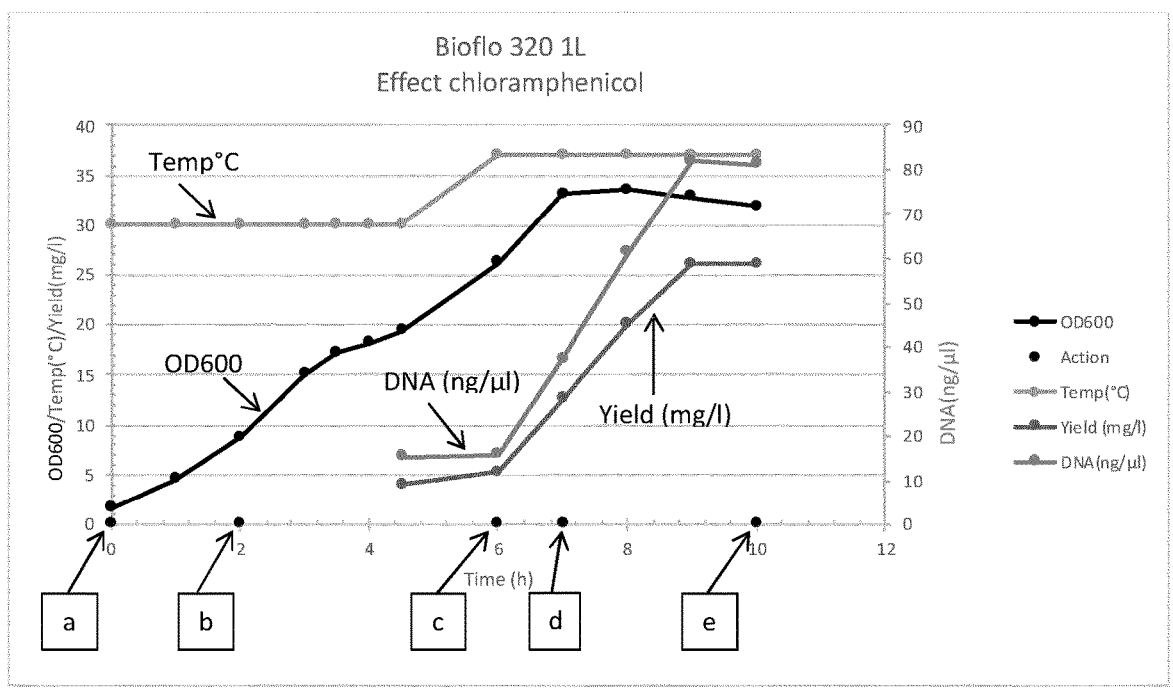
FIG. 7 represents the effect of chloramphenicol on plasmid production in a fermenter of 1 liter. Action (a) is seeding of bacterial cells: action (b) is starting glycerol feed: action (c) is inducing bacterial cells with IPTG: action (d) is adding chloramphenicol to the culture medium; and action (e) is harvesting the bacterial cells.

The bacteria were grown under these conditions for about 1.5 hours before being induced with IPTG (FIG. 7, action (c)). After about 2 hours post induction, chloramphenicol was added to i) suppress the bacterial internal machinery and focusing fully on the plasmid production and ii) to stabilize the oxygen need of the bacteria (FIG. 7, action (d)). About four hours after addition of chloramphenicol, the cells were harvested (FIG. 7, action (e)), and the yield was measured.

Bacterial growth reached a plateau very shortly after addition of chloramphenicol, which is indicative of the stop of the internal bacterial machinery (FIG. 7). At the same time, yield and DNA content increased exponentially, indicating that the bacteria mainly focused on plasmid production (FIG. 7). This led to the conclusion that addition of chloramphenicol is beneficial for the plasmid production.

Example 7. Switching from 30° C. To 37° C. Before Induction of the Inducible Origin of Replication is Beneficial for the Production Process Medium was inoculated with a glycerol stock of bacteria transformed with pViro Vet-4-YFV17D (FIG. 1) and incubated overnight in a shaker flask at 37° C. The next morning the OD$_{600}$ was measured, and the bacteria were diluted to an OD$_{600}$ of 0.1 in fresh medium supplemented with glucose in the fermenter vessel and incubated overnight at 30° C. (FIG. 8, action (a): seeding and action (b)).

In the morning, the feed was supplemented with glycerol instead of glucose not to inhibit the induction. In addition, the temperature was shifted from 30° C. to 37° C. to create the best environment for the production of the plasmid (FIG. 8, action (c)).

The bacteria were grown under these conditions for about 1.5 hours before being induced with IPTG (FIG. 5, action (d)). After about 2 hours post induction, chloramphenicol was added (FIG. 5, action (e)) and about 4 hours after that, the cells were harvested (FIG. 5, action (f)), and the yield was measured.

Figure 8:
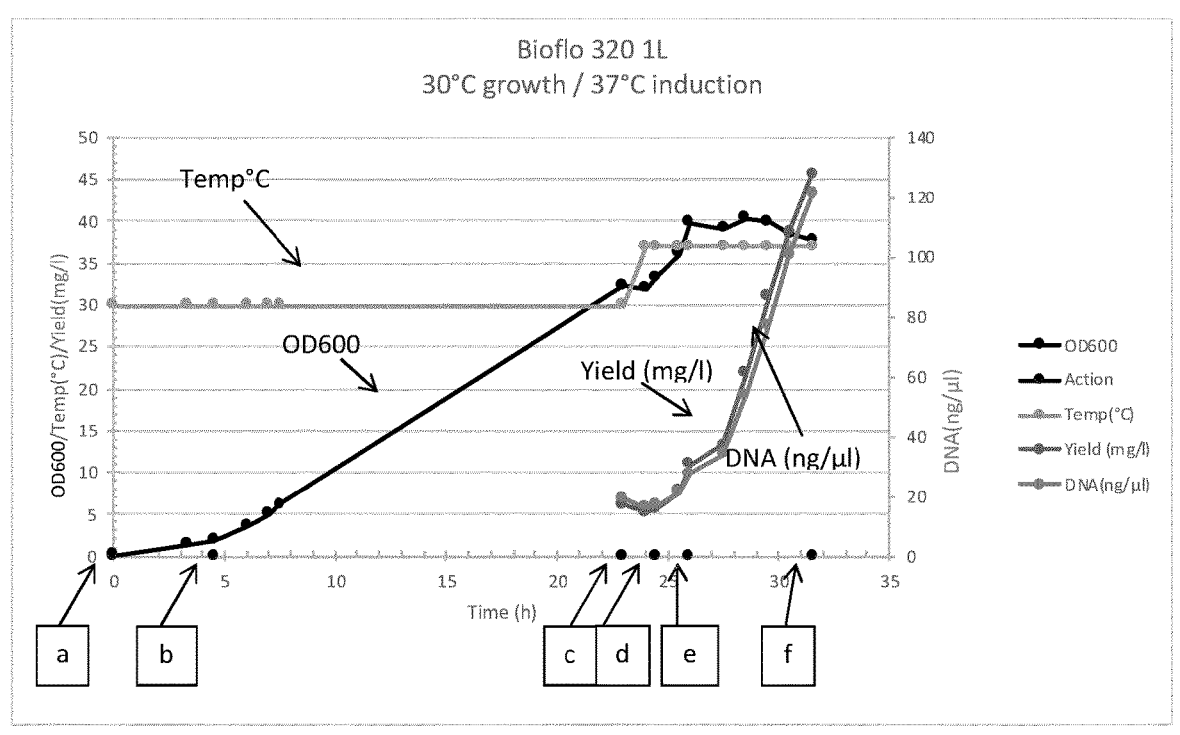
FIG. 8 represents the effect of temperature shift on the plasmid production in a fermenter of 1 liter. Action (a) is seeding of bacterial cells; action (b) is starting glucose feed.

The temperature shift let to an even higher yield as compared to the run presented in FIG. 7 (26 mg/l versus 45 mg/l), leading to the conclusion that switching from 30° C. to 37° C. is beneficial for the production process (FIG. 8).

The invention claimed is:

1. A vector with a size of at least 16 kb comprising an inducible origin of replication, wherein the inducible origin of replication comprises a nucleic acid sequence having at least 95% sequence identity with the nucleic sequence as set forth in SEQ ID NO 9.

2. The vector according to claim 1, wherein the inducible origin of replication comprises SEQ ID NO: 8.

3. The vector according to claim 1, wherein the inducible origin of replication comprises an A to G mutation at nucleic acid position 176 of the amino acid sequence as set forth in SEQ ID NO: 8 and/or a C to T mutation at nucleic acid position 397 of the amino acid sequence as set forth in SEQ ID NO: 8.

4. A method for the production of a vector with a size of at least 16 kb from bacterial cells, wherein the vector comprises an inducible origin of replication that comprises a nucleic acid sequence having at least 95% sequence identity with the nucleic sequence as set forth in SEQ ID NO: 9, the method comprising the consecutive steps of a) obtaining bacterial cells comprising the vector, b) inoculating culture medium with the bacterial cells comprising the vector, c) culturing the bacterial cells in the culture medium, d) adding one or more inducers of said inducible origin of replication to the culture medium when the bacterial culture has reached an optical density at 600 nm ($OD_{600}$) of at least 20, e) further culturing the bacterial cells in the culture medium, f) optionally separating the bacterial cells from the culture medium, and g) recovering the plasmid from the bacterial cells.

5. The method according to claim 4, further comprising adding an inhibitor of bacterial protein synthesis to the culture medium after step d) and before step f).

6. The method according to claim 4, wherein glucose and/or yeast extract are added to the culture medium during culturing the bacterial cells in the culture medium.

7. The method according to claim 6, wherein the culture medium comprising glucose is exchanged by culture medium comprising from 0.50% (v/v) to 2.0% (v/v) glycerol at least 30 minutes before adding the one or more inducers of plasmid replication to the culture medium.

8. The method according to claim 4, wherein step c) of culturing the bacterial cells in the culture medium is performed at a temperature of about 30° C. and wherein the temperature is increased from a temperature of about 30° C.

to a temperature from 36.0° C. to 38.0° C. at least two hours before adding the one or more inducers of plasmid replication to the culture medium.

9. The method according to claim 5, wherein the inhibitor of bacterial protein synthesis is chloramphenicol or spectinomycin.

10. The method according to claim 5, wherein the inhibitor of bacterial protein synthesis is added to the culture medium at least one hour after the addition of the one or more inducers of the inducible origin of replication.

11. The method according to claim 5, wherein the bacterial cells are separated from the culture medium at most 6 hours after addition of the one or more inducers of the inducible origin of replication.

12. An inducible origin of replication comprising a nucleic acid sequence having at least 95% sequence identity with the nucleic sequence as set forth in SEQ ID NO: 9 and wherein the inducible origin of replication comprises an A to G mutation at nucleic acid position 176 of the amino acid sequence as set forth in SEQ ID NO: 8 and/or a C to T mutation at nucleic acid position 397 of the amino acid sequence as set forth in SEQ ID NO: 8.

13. The method according to claim 4, wherein the inducible origin of replication comprises SEQ ID NO: 8.

14. The method according to claim 4, wherein the inducible origin of replication comprises an A to G mutation at nucleic acid position 176 of the amino acid sequence as set forth in SEQ ID NO: 8 and/or a C to T mutation at nucleic acid position 397 of the amino acid sequence as set forth in SEQ ID NO: 8.

* * * * *

SEQUENCE LISTING

<160> NUMBER OF SEQ ID NOS: 10

<210> SEQ ID NO 1
<211> LENGTH: 170
<212> TYPE: DNA
<213> ORGANISM: Artificial Sequence
<220> FEATURE:
<223> OTHER INFORMATION: RNAI

<400> SEQUENCE: 1
acagtatttg gtatctgcgc tctgctgaag ccagttacct tcggaaaaag agttggtagc      60
tcttgatccg gcaaacaaac caccgctggt agcggtggtt tttttgtttg caagcagcag     120
attacgcgca gaaaaaaagg atctcaagaa gatcctttga tcttttctac               170

<210> SEQ ID NO 2
<211> LENGTH: 67
<212> TYPE: DNA
<213> ORGANISM: Artificial Sequence
<220> FEATURE:
<223> OTHER INFORMATION: RNAI promoter

<400> SEQUENCE: 2
agcgaggtat gtaggcggtg ctacagagtt cttgaagtgg tggcctaact acggctacac      60
tagaagg                                                               67

<210> SEQ ID NO 3
<211> LENGTH: 59
<212> TYPE: DNA
<213> ORGANISM: Artificial Sequence
<220> FEATURE:
<223> OTHER INFORMATION: endogenous promoter of the RNAII pre-primer

<400> SEQUENCE: 3
gtagaaaaga tcaaaggatc ttcttgagat cctttttttc tgcgcgtaat ctgctgctt       59

<210> SEQ ID NO 4
<211> LENGTH: 70
<212> TYPE: DNA
<213> ORGANISM: Artificial Sequence
<220> FEATURE:
<223> OTHER INFORMATION: lac promoter

<400> SEQUENCE: 4
atgtaagtta gctcattcat taggcacccc aggctttaca ctttatgctt ccggctcgta      60
taatgtgtgg                                                            70

<210> SEQ ID NO 5
<211> LENGTH: 20
<212> TYPE: DNA
<213> ORGANISM: Artificial Sequence
<220> FEATURE:
<223> OTHER INFORMATION: LacO1 operator

<400> SEQUENCE: 5
attgtgagcg gataacaatt                                                 20

<210> SEQ ID NO 6
<211> LENGTH: 407
<212> TYPE: DNA
<213> ORGANISM: Artificial Sequence
<220> FEATURE:
<223> OTHER INFORMATION: truncated RNAII pre-primer

<400> SEQUENCE: 6

```
ctgctaatcc tgttaccagt ggctgctgcc agtggcgata agtcgtgtct taccgggttg        60
gactcaagac gatagttacc ggataaggcg cagcggtcgg gctgaacggg gggttcgtgc       120
acacagccca gcttggagcg aacgacctac accgaactga gataccataca gcgtgagcta       180 tgagaaagcg ccacgcttcc cgaagggaga aaggcggaca ggtatccggt aagcggcagg       240
gtcggaacag gagagcgcac gagggagctt ccaggggggaa acgcctggta tctttatagt       300
cctgtcgggt ttcgccacct ctgacttgag cgtcgatttt tgtgatgctc gtcaggggggg       360 cggagcctat ggaaaaacgc cagcaacgcg gcctttttac ggttcct                     407
```

```
<210> SEQ ID NO 7
<211> LENGTH: 407
<212> TYPE: DNA
<213> ORGANISM: Artificial Sequence
<220> FEATURE:
<223> OTHER INFORMATION: Mutated truncated RNAII pre-primer

<400> SEQUENCE: 7
ctgctaatcc tgttaccagt ggctgctgcc agtggcgata agtcgtgtct taccgggttg        60
gactcaagac gatagttacc ggatgaggcg cagcggtcgg gctgaacggg gggttcgtgc       120
acacagccca gcttggagcg aacgacctac accgaactga gataccataca gcgtgagcta       180 tgagaaagcg ccacgcttcc cgaagggaga aaggcggaca ggtatccggt aagcggcagg       240
gtcggaacag gagagcgcac gagggagctt ccaggggggaa acgcctggta tctttatagt       300
cctgttgggt ttcgccacct ctgacttgag cgtcgatttt tgtgatgctc gtcaggggggg       360 cggagcctat ggaaaaacgc cagcaacgcg gcctttttac ggttcct                     407
```

```
<210> SEQ ID NO 8
<211> LENGTH: 498
<212> TYPE: DNA
<213> ORGANISM: Artificial Sequence
<220> FEATURE:
<223> OTHER INFORMATION: iOri with truncated RNAII pre-primer

<400> SEQUENCE: 8
atgtaagtta gctcattcat taggcacccc aggctttaca ctttatgctt ccggctcgta        60
taatgtgtgg aattgtgagc ggataacaat tctgctaatc ctgttaccag tggctgctgc       120
cagtggcgat aagtcgtgtc ttaccgggtt ggactcaaga cgatagttac cggataaggc       180
gcagcggtcg gctgaacgg ggggttcgtg cacacagccc agcttggagc gaacgaccta       240
caccgaactg agatacctac agcgtgagct atgagaaagc gccacgcttc cgaagggag       300 aaaggcggac aggtatccgg taagcggcag ggtcggaaca ggagagcgca cgagggagct       360
tccaggggga aacgcctggt atctttatag tcctgtcggg tttcgccacc tctgacttga       420
gcgtcgattt ttgtgatgct cgtcaggggg gcggagccta tggaaaaacg ccagcaacgc       480 ggcctttttta cggttcct                                                    498
```

```
<210> SEQ ID NO 9
<211> LENGTH: 498
<212> TYPE: DNA
<213> ORGANISM: Artificial Sequence
<220> FEATURE:
<223> OTHER INFORMATION: iOri with mutated truncated RNAII pre-primer

<400> SEQUENCE: 9
atgtaagtta gctcattcat taggcacccc aggctttaca ctttatgctt ccggctcgta        60
```

-continued

```
taatgtgtgg aattgtgagc ggataacaat tctgctaatc ctgttaccag tggctgctgc       120
cagtggcgat aagtcgtgtc ttaccgggtt ggactcaaga cgatagttac cggatgaggc       180
gcagcggtcg ggctgaacgg ggggttcgtg cacacagccc agcttggagc gaacgaccta       240
caccgaactg agatacctac agcgtgagct atgagaaagc gccacgcttc ccgaagggag       300
aaaggcggac aggtatccgg taagcggcag ggtcggaaca ggagagcgca cgagggagct       360
tccaggggga aacgcctggt atctttatag tcctgttggg tttcgccacc tctgacttga       420
gcgtcgattt ttgtgatgct cgtcaggggg cggagccta tggaaaaacg ccagcaacgc        480 ggcctttta cggttcct                                                      498
```

```
<210> SEQ ID NO 10
<211> LENGTH: 644
<212> TYPE: DNA
<213> ORGANISM: Artificial Sequence
<220> FEATURE:
<223> OTHER INFORMATION: Full pMB1 (ColE1) ori

<400> SEQUENCE: 10
gtagaaaaga tcaaaggatc ttcttgagat ccttttttc tgcgcgtaat ctgctgcttg        60
caaacaaaaa aaccaccgct accagcggtg gtttgtttgc cggatcaaga gctaccaact       120 cttttttccga aggtaactgg cttcagcaga gcgcagatac caaatactgt ccttctagtg      180
tagccgtagt taggccacca cttcaagaac tctgtagcac cgcctacata cctcgctctg       240
ctaatcctgt taccagtggc tgctgccagt ggcgataagt cgtgtcttac cgggttggac       300
tcaagacgat agttaccgga taaggcgcag cggtcgggct gaacggggggg ttcgtgcaca      360 cagcccagct tggagcgaac gacctacacc gaactgagat acctacagcg tgagctatga       420
gaaagcgcca cgcttcccga agggagaaag gcggacaggt atccggtaag cggcagggtc       480
ggaacaggag agcgcacgag ggagcttcca gggggaaacg cctggtatct ttatagtcct       540
gtcgggtttc gccacctctg acttgagcgt cgattttgt gatgctcgtc aggggggcgg        600
agcctatgga aaaacgccag caacgcggcc tttttacggt tcct                        644
```